US008865901B2

(12) United States Patent
Hockenbery et al.

(10) Patent No.: US 8,865,901 B2
(45) Date of Patent: Oct. 21, 2014

(54) GAIN-OF-FUNCTION BCL-2 INHIBITORS

(75) Inventors: David Hockenbery, Seattle, WA (US); Julian Simon, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 13/437,795

(22) Filed: Apr. 2, 2012

(65) Prior Publication Data
US 2012/0252839 A1    Oct. 4, 2012

Related U.S. Application Data

(63) Continuation-in-part of application No. PCT/US2010/051208, filed on Oct. 1, 2010, and a continuation-in-part of application No. PCT/US2010/051201, filed on Oct. 1, 2010.

(60) Provisional application No. 61/248,304, filed on Oct. 2, 2009, provisional application No. 61/248,296, filed on Oct. 2, 2009.

(51) Int. Cl.
| | |
|---|---|
| A61K 31/47 | (2006.01) |
| C07D 217/22 | (2006.01) |
| C07D 401/12 | (2006.01) |
| C07C 251/86 | (2006.01) |
| C07D 271/08 | (2006.01) |
| C07D 213/77 | (2006.01) |
| C07C 323/20 | (2006.01) |
| C07C 235/60 | (2006.01) |

(52) U.S. Cl.
CPC ............ C07D 401/12 (2013.01); C07C 251/86 (2013.01); C07D 271/08 (2013.01); C07D 213/77 (2013.01); C07C 323/20 (2013.01); C07C 235/60 (2013.01); C07D 217/22 (2013.01)
USPC .......................................... 546/143; 514/310

(58) Field of Classification Search
None
See application file for complete search history.

(56) References Cited

U.S. PATENT DOCUMENTS

| | | | | |
|---|---|---|---|---|
| 3,455,940 | A | * | 7/1969 | Stecker .......................... 546/337 |
| 3,859,281 | A | * | 1/1975 | Bruce ............................ 544/272 |
| 4,006,239 | A | * | 2/1977 | Mayer et al. ................... 514/357 |
| 5,807,683 | A | | 9/1998 | Brenner et al. |
| 5,958,792 | A | | 9/1999 | Desai et al. |
| 6,001,879 | A | * | 12/1999 | Seitz et al. .................... 514/616 |
| 6,004,617 | A | | 12/1999 | Schultz et al. |
| 6,077,954 | A | | 6/2000 | Cook et al. |
| 6,503,933 | B1 | * | 1/2003 | Moloney et al. ............... 514/357 |
| 6,632,616 | B2 | | 10/2003 | Burke et al. |
| 6,680,299 | B2 | | 1/2004 | Or et al. |
| 6,680,322 | B2 | | 1/2004 | Castelhano et al. |
| 6,680,324 | B2 | | 1/2004 | Castelhano et al. |
| 7,071,158 | B2 | | 7/2006 | Chinery et al. |
| 2006/0084647 | A1 | | 4/2006 | Wang et al. |
| 2006/0094059 | A1 | | 5/2006 | Westwick et al. |
| 2009/0192220 | A1 | | 7/2009 | White et al. |

FOREIGN PATENT DOCUMENTS

| | | |
|---|---|---|
| WO | WO 02/089745 A2 | 11/2002 |
| WO | WO 2006/029850 A1 | 3/2006 |
| WO | WO 2006029850 A1 * | 3/2006 |
| WO | WO 2008/133884 A2 | 11/2008 |
| WO | WO 2009/008906 A2 | 1/2009 |
| WO | WO 2009/023299 A2 | 2/2009 |
| WO | WO 2010/083307 A2 | 7/2010 |
| WO | WO 2011/041731 A2 | 4/2011 |
| WO | WO 2011/041737 A2 | 4/2011 |

OTHER PUBLICATIONS

Silva, A., Mini-Reviews in Medicinal Chemistry, 2005, vol. 5, pp. 893-014.*
Sarkar, A. et al., Polyhedron 2006 vol. 25, pp. 1689-1694.*
Sarel, S. et al J. Med. Chem. 1999, vol. 42, pp. 242-248.*
CAPLUS 1967 441234.*
CAPLUS 1929 16201.*
CAPLUS 1912 6406.*
CAPLUS 1961:2396.*
Silverman, R. "The Organic Chemistry of Drug Design and Drug Action," 2004, Elsevier, pp. 29-32.*
CAPLUS 1991:42225.*
CAPLUS 1925:10458.*
CAPLUS 1933:26933.*
CAPLUS 1943:23113.*
Altschul, S.F. et al., "Basic Local Alignment Search Tool," J. Mol. Biol., 1990, 215:403-410.
Altschul, S.F. et al., "Gapped BLAST and PSI-BLAST: A New Generation of Protein Database Search Programs," Nucleic Acids Research, 1997, 25(17):3389-3402.
Barelier, Sarah et al., "Fragment-Based Deconstruction of Bcl-xL Inhibitors," Journal of Medicinal Chemistry, Mar. 25, 2010, 53(6):2577-2588.

(Continued)

Primary Examiner — Heidi Reese
(74) Attorney, Agent, or Firm — Baker & Hostetler LLP

(57) ABSTRACT

Compounds are described that are useful for treating an apoptosis-associated disease, which are specifically cytotoxic to tumor cells that are overexpressing Bcl-$x_L$, and are much less cytotoxic in isogenic cells that are not overexpressing Bcl-$x_L$. Also described is a method for treating an apoptosis-associated disease in a subject in need thereof, comprising administering to the subject a therapeutically effective amount of an active compound that is specifically cytotoxic to tumor cells that are overexpressing Bcl-$x_L$, and are much less cytotoxic in isogenic cells that are not overexpressing Bcl-$x_L$. Several scaffolds of active compounds are described.

11 Claims, 4 Drawing Sheets

(56) References Cited

OTHER PUBLICATIONS

Deye, J. et al., "Structure-Based Virtual Screening For Novel Inhibitors of the Sarco/Endoplamic Reticulum Calcium ATPase and Their Experimental Evaluation," Bioorganic & Medicinal Chemistry, Feb. 1, 2009, 17(3):1353-1360.

Feng, D. et al., "Progressive Sequence Alignment as a Prerequisite to Correct Phylogenetic Trees," J. Mol. Evol., 1987, 25:351-360.

Johnson, D.K. et al., "Cytotoxic Chelators and Chaltes 1. Inhibition of DNA synthesis in cultured rodent and human cells by aroylhydrazones and by a copper (II) complex of salicylaldehyde benzoyl hydrazone," Inorganica Chimica ACTA, 1982, 67:159-165.

Mohan, M. et al., "Synthesis, Characterization and Antitumor Activity of Iron (II) Iron (III) Complexes of 3- and 5-Substituted Salicylaldehyde Benzoyl Hydrazones," Inorganica Chimica Acta, 1987, 135:167-177.

Needleman, S.B. et al., "A General Method Applicable to the Search for Similarities in the Amino Acid Sequence of Two Proteins," J. Mol. Biol., 1970, 48:443-453.

Patil, S.A. et al., "Convenient and Efficient Suzuki-Miyaura Cross-Coupling Reactions Catalyzed by Palladium Complexes Containing $N,N,O$-Tridentate Ligands," Tetrahedron, Apr. 11, 2009, 65(15):2889-2897.

Pearson, W.R. et al., "Improved Tools for Biological Sequence Comparison," Proc. Natl. Acad. Sci. USA, Apr. 1988, 85:2444-2448.

Prescott, B. et al., "Potential Antitumor Agents: Derivatives of 2-Hydrazino-5-Nitropyridine," Journal of Pharmaceutical Sciences, Jan. 1, 1970, 59(1):101-103.

Sarel, S. et al., "Domain-Structured $N^1,N^2$-Derivatized Hydrazines as Inhibitors of Ribonucleoside Disphospate Reductase: Redox-Cycling Considerations," J. Med. Chem., Jan. 12, 1999, 42(2):242-248.

Sarkar, A. et al., "Dioxovandium(V) Complexes with N,N,O.-donor Monoanionic Ligands: Synthesis, Structure and Properties," Polyhedron, Apr. 11, 2007, 26(6):1205-1210.

Wu, G.Y. et al., "Receptor-Mediated in vitro Gene transormation by a Soluble DNA Carrier System," Journal of Biological Chemistry, Apr. 5, 1987, 262:4429-4432.

Zhang, Z. et al., "Protein Sequence Similarity Searches Using Patterns as Seeds," Nucleic Acids Research, 1998, 26(17):3986-3990.

Pliss, G.B. et al.; Ceasar Accession No. 1319; "Inhibition of O-Aminoazotoluene-Induced Tumors by Antioxidants"; Chemical Abstracts Services, Columbus, Ohio; 1974 20(7);47-49.

\* cited by examiner

GAIN-OF-FUNCTION BCL-2 INHIBITORS

CROSS REFERENCE TO RELATED APPLICATIONS

This application is a continuation-in-part of International Patent Application No. PCT/US2010/051201 filed Oct. 1, 2010 and International Patent Application No. PCT/US2010/051208 filed Oct. 1, 2010, which claim the benefit of U.S. Provisional Application Nos. 61/248,296 filed Oct. 2, 2009 and 61/248,304 filed Oct. 2, 2009 respectively; each of which is hereby incorporated by reference in its entirety.

TECHNICAL FIELD

The present invention relates to compounds for modulating apoptosis in cells over expressing Bcl-2 family member proteins. The present invention also relates to pharmaceutical compositions containing these compounds and methods of using the compounds.

BACKGROUND

Antiapoptotic functions of Bcl-2, Bcl-$x_L$, and potentially other family members, including Mcl-1 and Bcl-w, confer marked resistance to the cytotoxic effects of available anticancer agents. In addition, Bcl-2 survival proteins are overexpressed in comparison to normal tissue counterparts in a significant subset of common cancers. Low-basal Bcl-$x_L$ expression is a strong negative predictor of cell survival with diverse classes of chemotherapeutic agents in the sixty cell lines included in the National Cancer Institute (NCI) anticancer drug screen. For these reasons, small-molecule inhibitors of Bcl-2 and Bcl-$x_L$ are being considered as a goal for molecularly targeted cancer therapy. A major challenge in developing therapeutic inhibitors for Bcl-2-related survival proteins is the expression of these targets in many normal cell types (Hockenbery et al. *Proc Natl Acad Sci USA* 1991; 88:6961-65; Park J R, et al. *Blood* 1995; 86:868-76). The dependence of healthy tissues on the Bcl-2 family of antiapoptotic proteins for cell viability may narrow the therapeutic window for these agents. 2-methoxy antimycin A (2-MeAA) represents the first of a novel class of inhibitors that display gain-of-function cytotoxicity, defined as enhanced killing in a cell line overexpressing a Bcl-2 survival protein target compared with an isogenic control cell line. (Manion et al. *Current Opinion in Investigational Drugs* 2006; 7:1077-84; and Schwartz et al. *Mol Cancer Ther* 2007; 6:2073-80).

Based on the gain-of-function model, cancer cells with high endogenous levels of Bcl-$x_L$ would be predicted to exhibit greater sensitivity to 2-MeAA than cancers with low Bcl-$x_L$ expression. Bcl-$x_L$ expression shows a positive correlation with sensitivity to 2-MeAA when comparing five cancer cell lines with the highest Bcl-$x_L$ mRNA expression in the NCI anticancer drug screen to five cell lines with lowest Bcl-$x_L$ expression, i.e., 2-MeAA is most cytotoxic against cells with the highest Bcl-$x_L$ expression. In contrast Bcl-$x_L$ expression levels show a negative correlation with standard therapeutic agents, i.e., standard therapeutics are less cytotoxic against cells with high Bcl-$x_L$ expression levels. Schwartz 2007. Mesothelioma cell lines with high expression of Bcl-$x_L$ and Bcl-2 show in vitro and in vivo sensitivity to 2-MeAA. Thus, this class of activity (i.e., gain-of-function inhibitors) may expand the potential of Bcl-2 inhibitors beyond chemosensitization while also providing an improved therapeutic index.

Overexpression of Bcl-$x_L$ in multiple cancers correlates with resistance to chemotherapy and radiation therapy, and provides a rationale for development of small-molecule Bcl-$x_L$ inhibitors. Based on knockout studies, non-neoplastic cells also require Bcl-$x_L$ survival functions, particularly when challenged with cytotoxic agents. One Bcl-$x_L$ inhibitor, 2-MeAA, was found to be cytotoxic in cells with excess exogenous Bcl-$x_L$ but had less cytotoxicity in isogenic cell line pairs having basal levels of Bcl-$x_L$ expression (Tzung et al. *Nature New Biol* 2001; 3:183-91; Hockenbery et al. U.S. Pat. No. 7,241,804, issued Jul. 10, 2007; and Hockenbery et al. US 2005/0239873, filed Jan. 14, 2005). This selectivity, characteristic of a gain-of-function mechanism, is not shared by other known Bcl-$x_L$ inhibitors, including BH3I-2, HA14-1, ABT-737, gossypol, or the stapled BH3 helical peptide SAHB-BID (Schwartz 2007). Also in contrast to other Bcl-$x_L$ inhibitors, gain-of-function Bcl-$x_L$ inhibitors can be combined with a standard inducer of apoptosis, staurosporine, to enhance selective cytotoxicity toward Bcl-$x_L$-overexpressing cells. (Id.)

Small-molecule, gain-of function Bcl-$x_L$ inhibitors, were identified showing characteristic preferential cytotoxicity against cells overexpressing Bcl-$x_L$ cells. These include NSC 310343 inhibitor with gain-of-function activity, (Id.) and others. (Wu et al. WO 08/021,250, filed Aug. 10, 2007, and Schwartz et al. WO 08/021,211, filed Aug. 10, 2007). Other compounds have been shown to be inhibitors of proliferative disorders, including cancer (Hirth et al. U.S. Pat. No. 5,700,823; Beachy et al. WO 05/033048; Okada et al. U.S. Pat. No. 5,807,880). Methods for detecting cell apoptosis and methods for screening potential therapeutic compounds which inhibit or stimulate apoptosis have been described (Siman et al. U.S. Pat. No. 6,048,703; and Soto et al. U.S. Pat. No. 6,939,679; Tomei et al. WO 99/03054).

It would be desirable to identify other compounds that may be effective in inducing apoptosis in cells where apoptosis is inappropriately regulated while causing minimal cytotoxicity in normal, otherwise isogenic cells.

DETAILED DESCRIPTION OF THE DRAWINGS

DETAILED DESCRIPTION OF ILLUSTRATIVE EMBODIMENTS

Figure 1:
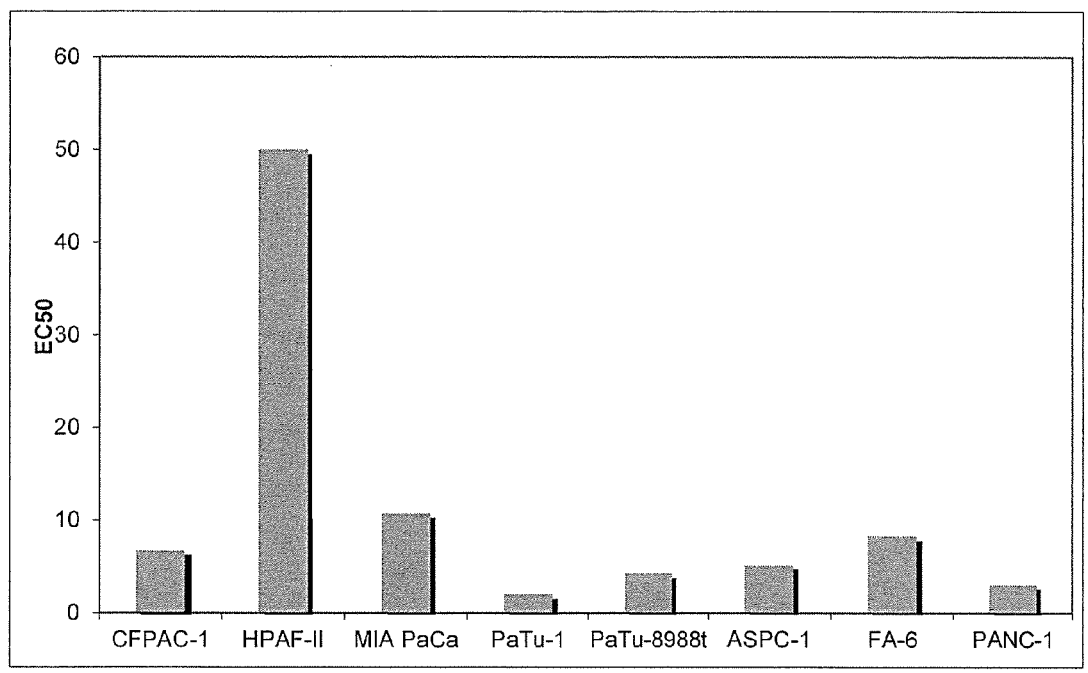
FIG. 1 shows EC50 values for FH279 in micromolar units as measured in the following cell lines: CFPAC-1, HPAF-II MIA PaCa, PaTu-1, PaTu-8988t, ASPC-1, FA-6, and PANC-1, as described in Examples 4 and 20.

The present invention will now be described with respect to embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art. The terminology used in the description of the invention herein is for the purpose of describing particular embodiments only and is not intended to be limiting of the invention.

As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this invention belongs. All publications, patent applications, patents, and other references mentioned herein are incorporated by reference in their entirety.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms.

"Alkyl" as used herein alone or as part of another group, refers to a straight or branched chain hydrocarbon containing from 1 to 10 carbon atoms. In some embodiments, the alkyl employed in the invention contains 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, -tert-butyl, and the like. The term "alkyl" or "lower alkyl" is intended to include both substituted and unsubstituted alkyl or lower alkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$-, haloalkyl-$S(O)_m$-, alkenyl-$S(O)_m$-, alkynyl-$S(O)_m$-, cycloalkyl-$S(O)_m$-, cycloalkylalkyl-$S(O)_m$-, aryl-$S(O)_m$-, arylalkyl-$S(O)_m$-, heterocyclo-$S(O)_m$-, heterocloalkyl-$S(O)_m$-, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in lower alkenyl 1 to 4 carbon atoms) which include 1 to 4 double bonds in the normal chain. In some embodiments, the alkenyl employed in the invention contains 1 to 6 carbon atoms. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or lower alkenyl unless otherwise indicated and these groups may be substituted with groups as described in connection with alkyl and lower alkyl above.

"Alkynyl" as used herein alone or as part of another group, refers to a straight or branched chain hydrocarbon containing from 1 to 10 carbon atoms (or in lower alkynyl 1 to 4 carbon atoms) which include 1 to 4 triple bond in the normal chain. In some embodiments, the alkynyl employed in the invention contain 1 to 6 carbon atoms. Representative examples of alkynyl include, but are not limited to, 2-propynyl, 3-butynyl, 2-butynyl, 4-pentynyl, 3-pentynyl, and the like. The term "alkynyl" or "lower alkynyl" is intended to include both substituted and unsubstituted alkynyl or lower alkynyl unless otherwise indicated and these groups may be substituted with the same groups as set forth in connection with alkyl and lower alkyl above.

"Cycloalkyl", as used herein alone or as part of another group, refers to groups having 3 to 10 carbon atoms. In some embodiments, the cycloalkyl employed in the invention has 3 to 8 carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or heterocyclic moieties, may optionally be substituted with the same groups as set forth in connection with alkyl and lower alkyl above. "Heterocycloalkyl" or "heterocycle", as used herein alone or as part of another group, refers to a non-aromatic 3-, 4-, 5-, 6-, 7-, or 8-membered ring or a polycyclic group, including, but not limited to a bi- or tri-cyclic group comprising fused six-membered rings having between one and four heteroatoms independently selected from oxygen, sulfur and nitrogen, wherein (i) the nitrogen and sulfur heteroatoms may be optionally oxidized, (ii) the nitrogen heteroatom may optionally be quaternized, and (iii) may form a spiro ring or be fused with a cycloalkyl, aryl, heterocyclic ring, benzene or a heteroaromatic ring. In some embodiments, the heterocycle employed in the invention have 3 to 10 carbon atoms. Representative heterocycles include, but are not limited to, 1,4-dioxa-8-azaspiro[4,5]decane, morpholine, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazolone, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, benzimidazole, benzothiazole, benzothiadiazole, benzothiophene, benzoxadiazole, benzoxazole, benzofliran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with the same groups as set forth in connection with alkyl and lower alkyl above.

"Aryl" as used herein alone or as part of another group, refers to a monocyclic carbocyclic ring system or a bicyclic carbocyclic fused ring system having one or more aromatic rings. In some embodiments, the aryl employed in the invention has 3 to 14 carbon atoms. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be optionally substituted with the same groups as set forth in connection with alkyl and lower alkyl above.

"Aryl alkyl" as used herein alone or as part of another groups refers to an aryl group, as defined herein, appended to the parent molecular moiety through an alkyl group, as defined herein. Representative examples of aryl alkyl include, but are not limited to, benzyl, 2-phenylethyl, 3-phenylpropyl, 2-naphth-2-ylethyl, and the like.

"Heteroaryl" as used herein alone or as part of another group, refers to a cyclic, aromatic hydrocarbon in which one or more carbon atoms have been replaced with heteroatoms such as O, N, and S. If the heteroaryl group contains more than one heteroatom, the heteroatoms may be the same or different. In some embodiments, the heteroaryl employed in the invention have 3 to 14 carbon atoms. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. In some embodiments, heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible. For example, the heteroatom N or S may be substituted with one or two oxo groups, which may be shown as =O.

"Alkoxy" (or "alkyloxy"), or "thioalkyl", as used herein alone or as part of another group, refers to an alkyl or lower alkyl group appended to the parent molecular moiety through an oxygen or sulfur atom. In some embodiments, the alkoxy or thioalkyl group contains 1-10 carbon atoms. In other embodiments, the alkyl, alkenyl, and alkynyl groups employed in the invention contain 1-8 carbon atoms. In still other embodiments, the alkyl group contains 1-6 carbon atoms. In yet other embodiments, the alkyl group contains 1-4 carbon atoms. Representative examples, of alkoxy, include but are not limited to, methoxy, ethoxy, propoxy, isopropoxy, n-butoxy, tert-butoxy, neopentoxy and n-hexoxy and the like. Representative examples of thioalkyl include, but are not limited to, methylthio, ethylthio, propylthio, isopropylthio, n-butylthio, and the like.

"Halo" as used herein alone or as part of another group, refers to any suitable halogen, including —F, —Cl, —Br, and —I.

"Amine" or "amino group", as used herein alone or as part of another group, refers to the radical —NH2. An "optionally substituted" amine refers to —NH2 groups wherein none, one or two of the hydrogen(s) is replaced by a suitable substituent. Disubstituted amines may have substituents that are bridging, i.e., form a heterocyclic ring structure that includes the amine nitrogen.

"Aminoalkyl group" is intended to mean the radical —NHR3, where R3 is an alkyl group.

"Haloalkyl", as used herein alone or as part of another group, refers to an alkyl group having one, two, or three halogen atoms attached thereto and is exemplified by such groups as chloromethyl, bromoethyl, trifluoromethyl, and the like.

The term "apoptosis" refers to a regulated network of biochemical events which lead to a selective form of cell suicide, and is characterized by readily observable morphological and biochemical phenomena, such as the fragmentation of the deoxyribo-nucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient and the like.

The term "preferentially induce" apoptosis refers to at least a 5-fold greater stimulation of apoptosis, at a given concentration of an agent, including a 2-methoxy antimycin derivative, in cells that over-express a Bcl-2 family member protein as compared with cells that do not over-express the Bcl-2 family member protein (e.g., a 5-fold lower $LD_{50}$ or IC50).

The term "substantially non-toxic" refers to an agent, including 2-MeAA, that induces apoptosis in at least about 50 percent of cells that over-express a Bcl-2 family member protein, but does not induce apoptosis in more than about 5%, more preferably less than 1%, of cells that do not over-express the Bcl-2 family member protein.

The term "Bcl-2 family member protein(s)" refers to an evolutionarily conserved family of proteins characterized by having one or more amino acid homology domains, BH1, BH2, BH3, and/or BH4. The Bcl-2 family member proteins include Bcl-2, Bcl-$x_L$, Bcl-w, Al, McI-1, Bax, Bak, Bad, Bcl-xs, Bid, and the like. The "Bcl-2 family member proteins" further include those proteins, or their biologically active fragments, that have at least 70%, preferably at least 80%, and more preferably at least 90% amino acid sequence identity with a Bcl-2 family member protein.

The term "anti-apoptotic Bcl-2 family member protein" refers to Bcl-2, Bcl-$x_L$, BCI-w, Al, McI-1, and other proteins characterized by having one or more amino acid homology domains, BH1, BH2, BH3, and/or BH4, and that promote cell survival by attenuating or inhibiting apoptosis. The "anti-apoptotic Bcl-2 family member proteins" further include those proteins, or their biologically active fragments, that have at least 70%, preferably at least 80%, and more preferably at least 90% amino acid sequence identity with an anti-apoptotic Bcl-2 family member protein.

The terms "identity" or "percent identity" in the context of two or more nucleic acid or polypeptide sequences, refer to two or more sequences or subsequences that are the same or have a specified percentage of amino acid residues or nucleotides that are the same, when compared and aligned for maximum correspondence, as measured using either a PILEUP or BLAST sequence comparison algorithm (see, e.g., J. MoI. Evol. 35:351-360, 1987; Higgins and Sharp, CABIOS 5:151-153, 1989; Altschul et al, J. MoI Biol 215: 403-410, 1990; Zhang et al, Nucleic Acid Res. 26:3986-3990, 1998; Altschul et al, Nucleic Acid Res. 25:3389-33402, 1997). Optimal alignment of sequences for comparison can be conducted, e.g., by the local homology algorithm of Smith and Waterman, Adv. Appl. Math. 2:482, 1981, by the homology alignment algorithm of Needleman and Wunsch, J. Mol. Biol. 48:443, 1970, by the search for similarity method of Pearson and Lipman, Proc. Nat. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see, generally, Ausubel et al, supra).

In the context of Bcl-2 family member proteins, "correspondence" of one polypeptide sequence to another sequence (e.g., regions, fragments, nucleotide or amino acid positions, or the like) is based on the convention of numbering according to nucleotide or amino acid position number, and then aligning the sequences in a manner that maximizes the number of nucleotides or amino acids that match at each position, as determined by visual inspection or by using a sequence comparison algorithm such as, for example, PILEUP (see, e.g., supra; Higgins & Sharp, supra) or BLAST (see, e.g., Altschul et al., supra; Zhang et al., supra; Altschul et al., supra). For example, a mutant Bcl-2 family member amino acid sequence having one or more amino acid substitutions, additions, or deletions as compared to the wild-type protein may correspond to a second Bcl-2 family member amino acid sequence (e.g., the wild-type sequence or a functionally equivalent variant thereof) according to the convention for numbering the second Bcl-2 family member sequence, whereby the mutant sequence is aligned with the second Bcl-2 family member sequence such that at least 50%, typically at least 60%, more typically, at least 70%, preferably at least 80%, more preferably at least 90%, and even more preferably at least 95% of the amino acids in a given sequence of at least 20 consecutive amino acids are identical. Because not all positions with a given "corresponding region" need be identical, non-matching positions within a corresponding region are herein regarded as "corresponding positions."

As used herein, a single amino acid substitution in one ("first") mutant Bcl-2 family member protein "corresponds" to a single amino acid substitution in a second mutant Bcl-2 family member protein (e.g., Bcl-$x_L$) where the corresponding substituted amino acid positions of the first and second mutant proteins are identical.

In the context of Bcl-2 family member protein mutants, the phrase "no substantial effect on tertiary protein structure relative to the corresponding wild-type Bcl-2 family member protein" or "no substantial alteration of tertiary protein structure relative to the corresponding wild-type Bcl-2 family member protein" means that, when a Cα trace providing a position for each Cα carbon of the mutant protein is superimposed onto a Cα trace of the corresponding wild-type protein and an α carbon root mean square (RMS) difference root mean square deviation (RMSD) is calculated; i.e., the deviation of the mutant structure from that of the wild-type structure), the RMSD value is no more than about 1.0 Å when calculated using the same structural modeling method, typically no more than about 0.75 Å, even more typically no more than about 0.5 Å, preferably no more than about 0.35 Å, and even more preferably no more than about 0.25 Å.

The terms "biologically active" or "biological activity" refer to the ability of a molecule to modulate apoptosis, such as by binding to a Bcl-2 family member protein. A biologically active molecule can modulate apoptosis by causing a change in the mitochondrial proton motive force gradient, by causing a change in mitochondrial swelling or the morphological characteristics of mitochondria, by affecting the release of a reporter molecule, e.g., rhodamine 123 or calcein, from mitochondria or vesicles comprising a pore-forming anti-apoptotic Bcl-2 family member protein, or by causing any other morphological change associated with apoptosis.

The term "effective amount" or "effective" is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. For example, an amount of an agent that effectively modulates the apoptotic state of an individual cell such that apoptosis is induced and/or the inappropriately regulated cell death cycle in the cell returns to a normal state. As is generally understood in the art, the dosage will vary depending on the administration routes, symptoms and body weight of the patient but also depending upon the compound being administered. The terms "therapeutically useful" and "therapeutically effective" refer to an amount of an agent that effectively modulates the apoptotic state of an individual cell such that apoptosis is induced and/or the inappropriately regulated cell death cycle in the cell returns to a normal state.

The terms "diagnostically useful" and "diagnostically effective" refer to an agent (e.g., an antimycin derivative) for detecting the induction or inhibition of apoptosis in a subject. These terms further include molecules useful for detecting diseases associated with apoptosis, or the susceptibility to such diseases, and for detecting over-expression or under-expression of a Bcl-2 family member protein.

The terms "over-expression" and "under-expression" refer to an increase or decrease, respectively, in the levels of a Bcl-2 family member protein in a cell relative to the level of such a protein found in the same cell or a closely related non-malignant cell under normal physiological conditions. The term "apoptosis-associated disease" includes diseases, disorders, and conditions that are linked to an increased or decreased state of apoptosis in at least some of the cells of a subject. Such diseases include neoplastic disease (e.g., cancer and other proliferative diseases), tumor formation, arthritis, inflammation, autoimmune disease, human immunodeficiency virus (HIV) immunodeficiency syndrome, neurodegenerative diseases, myelodysplastic syndromes (such as aplastic anemia), ischaemic syndromes (such as myocardial infarction), liver diseases which are induced by toxins (such as alcohol), alopecia, damage to the skin due to UV light, lichen planus, atrophy of the skin, cataract, and graft rejections and other premalignant and noneoplastic hyperproliferative disorders. Apoptosis-associated diseases further include drug resistance associated with increased or decreased levels of an anti-apoptotic Bcl-2 family member protein as well as multiple chemotherapeutic drug resistance.

A "combinatorial library" is a collection of compounds in which the compounds comprising the collection are composed of one or more types of subunits. The subunits can be selected from natural or unnatural moieties, including diener, benzene compounds, cycloalkanes, lactones, dilactones, amino acids, alkanes, and the like. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules, which are different from each other (i.e., five (5) different molecules and not five (5) copies of the same molecule). Each of the different molecules (different basic structure and/or different substituents) will be present in an amount such that its presence can be determined by some means (e.g., can be isolated, analyzed, detected with a binding partner or suitable probe). The actual amounts of each different molecule needed so that its presence can be determined can vary due to the actual procedures used and can change as the technologies for isolation, detection and analysis advance. When the molecules are present in substantially equal molar amounts, an amount of about 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin, and the like. After attachment of the starting compound, substituents are attached to the starting compound. For example, the starting compound can comprise the dilactone moiety, or a precursor thereof. Substituents are added to the starting compound, and can be varied by providing a mixture of reactants comprising the substituents. Examples of suitable substituents include, but are not limited to, the following:

(1) hydrocarbon substituents, i.e., aliphatic (e.g., alkyl or alkenyl), alkicyclic (e.g., cycloalkyl, cycloalkenyl) substituents, aromatic, aliphatic and alkicyclic-substituted aromatic nuclei, and the like, as well as cyclic substituents;

(2) substituted hydrocarbon substituents, i.e., those substituents containing nonhydrocarbon radicals which do not alter the predominantly hydrocarbon substituent; those skilled in the art will be aware of such radicals (e.g., halo (especially chloro and fluoro), alkoxy, mercapto, alkylmercapto, nitro, nitroso, sulfoxy, and the like);

(3) hetero substituents, that is, substituents which will, while having predominantly hydrocarbyl character, contain other than carbon atoms. Suitable heteroatoms will be apparent to those of ordinary skill in the art and include, e.g., sulfur, oxygen, nitrogen, and such substituents as pyridyl, furanyl, thiophenyl, imidazolyl, and the like. Heteroatoms, and typically no more than one, will be present for each carbon atom in the hydrocarbon-based substituents. Alternatively, there may be no such radicals or heteroatoms in the hydrocarbon-based substituent and it will, therefore, be purely hydrocarbon.

Methods of making combinatorial libraries are known in the art, and include for example, the following: U.S. Pat. Nos. 5,958,792; 5,807,683; 6,004,617; 6,077,954.

Active Compounds

One embodiment of the invention is an isolated compound consisting of Formula I

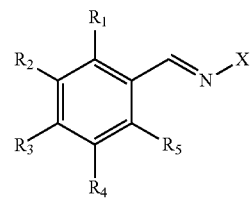

I wherein:
$R_1$ is hydroxyl, halide, or alkoxy;
$R_2$ is H, $NO_2$, halide, alkyl, or alkoxy;
$R_3$ is H, or alkyl;
$R_4$ is H, halide, or alkyl
$R_5$ is H, halide, or hydroxyl; and
X is —NH—$R_6$; —[C═O]—$R_6$; or —NH—[C═O]—$R_6$—;
wherein $R_6$ is

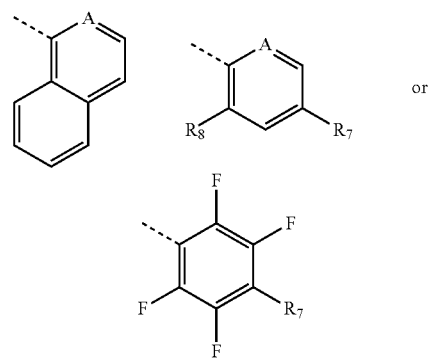

A is CH or N;
$R_7$ is H, $NO_2$, or $CF_3$; and
$R_8$ is H or halide;
or a salt, or a prodrug or a prodrug salt; or a hydrate or a solvate of any of the foregoing. Preferably
$R_1$ is hydroxyl, Cl, methoxyl;
$R_2$ is H, $NO_2$, Cl, Br, t-butyl, or methoxyl;
$R_3$ is H, methyl, or t-butyl;
$R_4$ is H, Cl, Br, t-butyl, or methyl;
$R_5$ is H, Cl, or hydroxyl;
$R_7$ is H, $NO_2$, or $CF_3$; and
$R_8$ is H, or Cl.
Most preferably when X is —NH—$R_6$, $R_6$ is

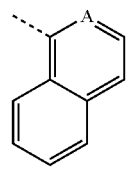

and A is N; or

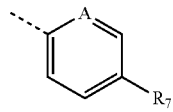

and A is CH or N, and R$_7$ is H, NO$_2$, or CF$_3$. Preferably, when X is [C=O]—R$_6$—, R$_6$ is

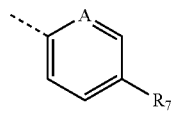

and A is CH or N; or R$_6$ is

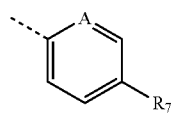

and R$_7$ is H or CF$_3$; or R$_6$ is

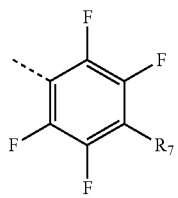

and wherein R$_7$ is CF$_3$. Preferably, when X is —NH—[C=O]—R$_6$—, R$_6$ is

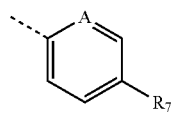

and A is CH; or R$_6$ is

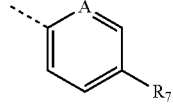

and R$_7$ is H.

Another embodiment of the invention is a compound consisting of the structure of Formulas II or III,

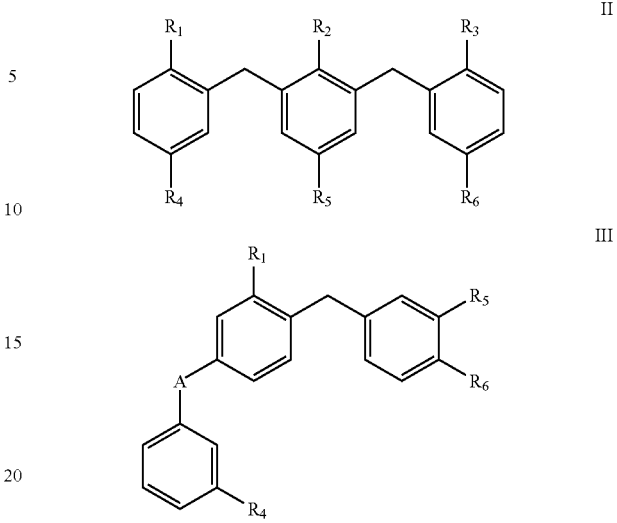

wherein;

R$_1$, R$_2$, and R$_3$ are each independently H, OH, alkoxy, or OAc;
R$_4$, R$_5$, and R$_6$ are each independently H, alkyl, or halide and
A is CH$_2$, O, S, SO, SO$_2$, or none.

Preferably,
R$_1$ is H, OH, OMe, OAc, or O(C=O)CMe$_2$;
R$_2$ is H, OH, OMe, or OAc;
R$_3$ is H, OH, OMe, OAc, or O(C=O)CMe$_2$;
R$_4$ is H, Me, t-butyl, or Cl;
R$_5$ is H, Me, or Cl;
R$_6$ is H; and
A is O or CH$_2$.

Another aspect of the invention is a compound selected from the group consisting of:

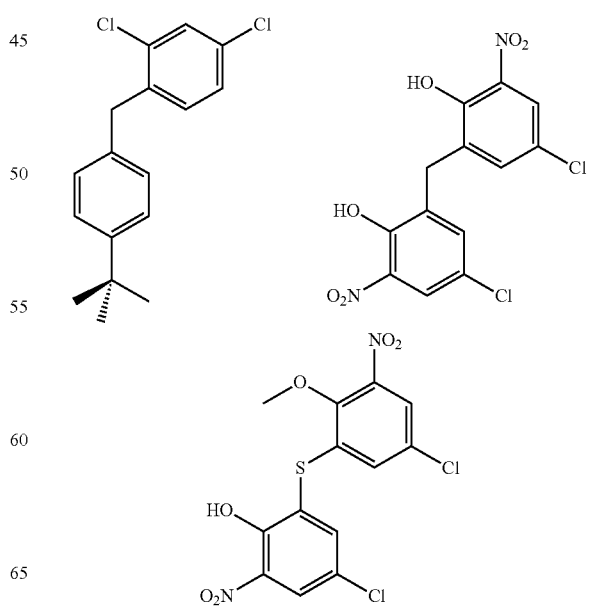

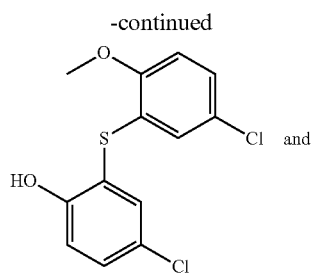

and

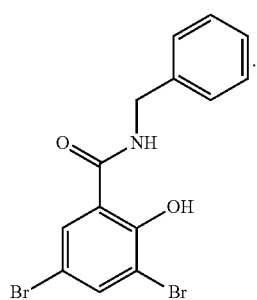

Another aspect of the invention is a compound consisting of formula:

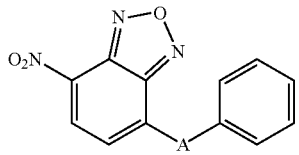

in which A is —S—CH2-; —SO—CH2-; or —SO2-.

Another aspect of the invention is a compound consisting of formula

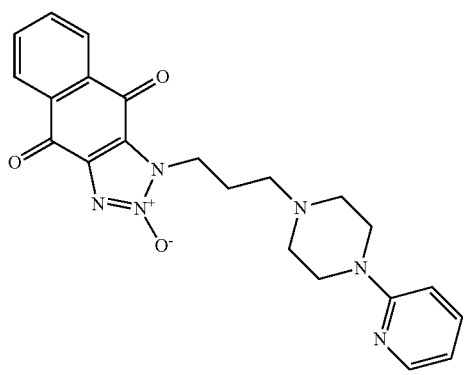 [SMILES: O=C1c2ccccc2C(=O)c2c1n[n+]([O-])n2CCCN1CCN(c2ccccn2)CC1]

Another aspect of the invention is any one of the above compounds in which the active compound has an IC50 less than about 5 micromole/liter (5 µM) in cells overexpressing Bcl-$x_L$, and at least about 20-fold less cytotoxic in isogenic cells that are not overexpressing Bcl-$x_L$. Examples of such compound are:

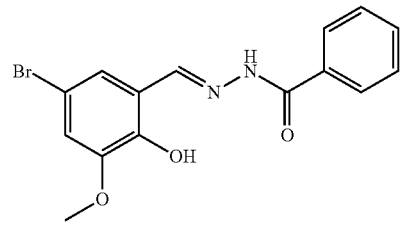

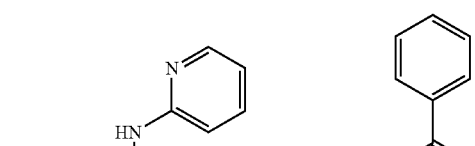

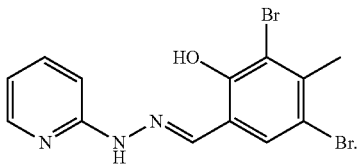

and

A most preferred embodiment is an active compound that has an IC50 less than about 3 µM in cells overexpressing Bcl-$x_L$. Examples of such compounds are:

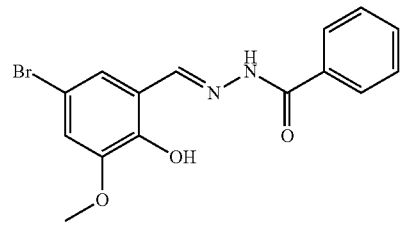

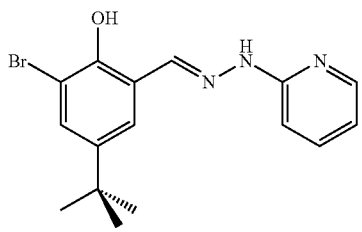

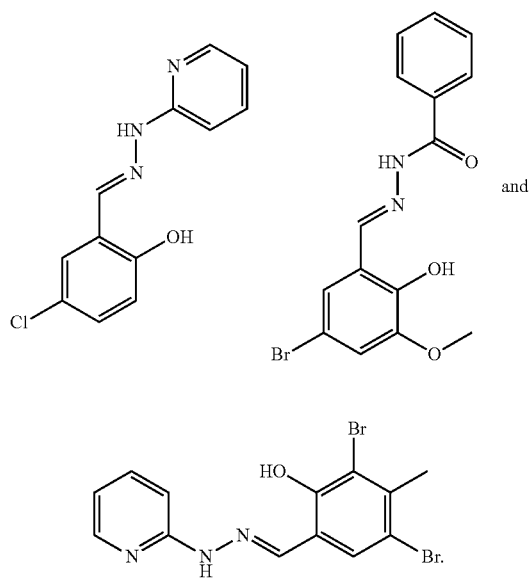
Another aspect of the invention is a compound described above in which the active compound has an IC50 less than about 5 micromole/liter (5 μM) in cells overexpressing Bcl-$x_L$, and at least about 10-fold less cytotoxic in isogenic cells that are not overexpressing Bcl-$x_L$. Examples of such compounds include:
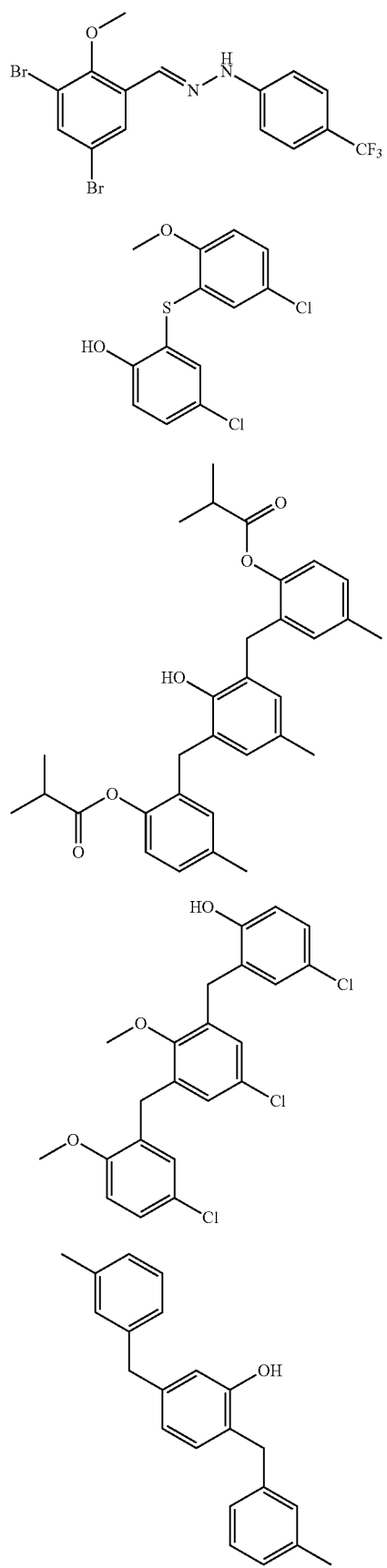

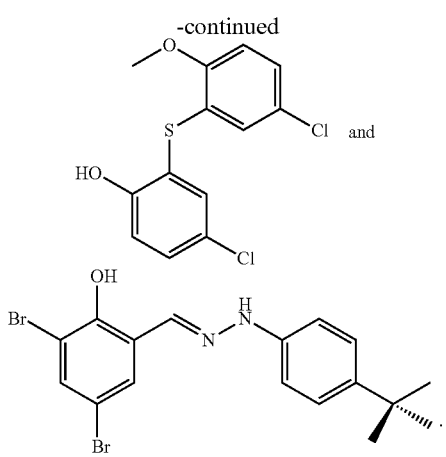

Most preferably the compound selected from this group has an IC50 less than about 3 µM in cells overexpressing Bcl-x$_L$. Examples of such compound include:

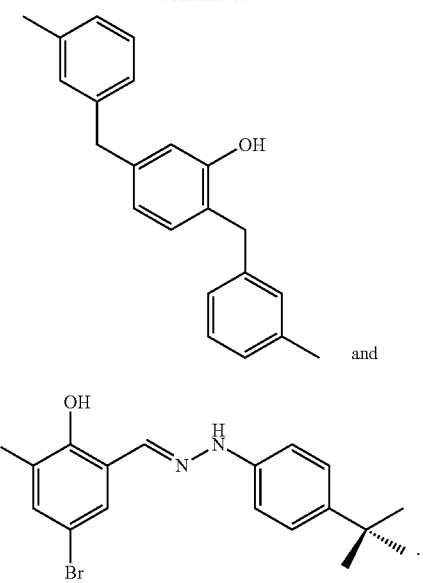

Another aspect of the invention is a compound described above in which the active compound has an IC50 less than about 5 micromole/liter (5 µM) in cells overexpressing Bcl-x$_L$, and at least about 5-fold less cytotoxic in isogenic cells that are not overexpressing Bcl-x$_L$. Examples of such compounds include:

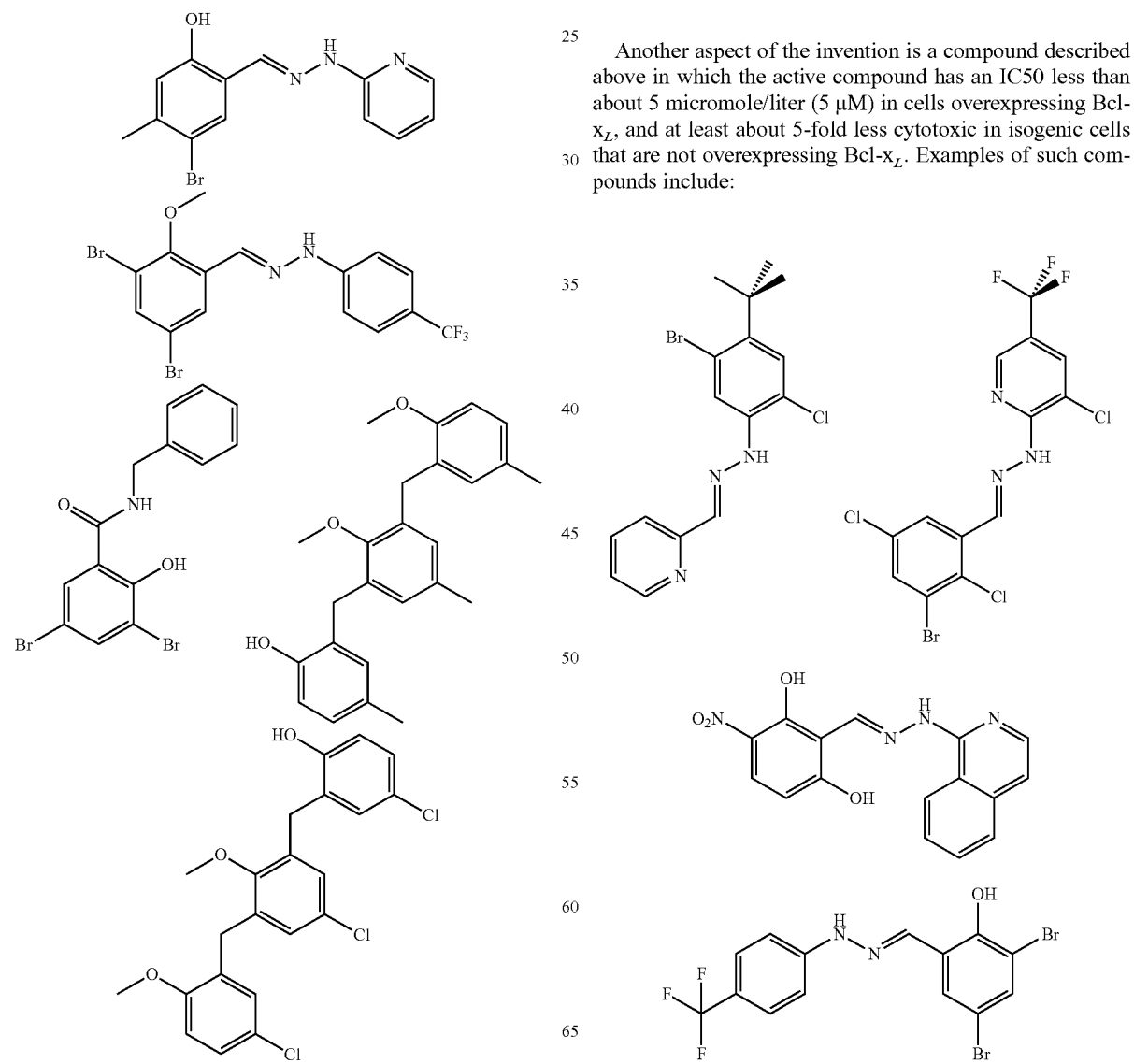

-continued
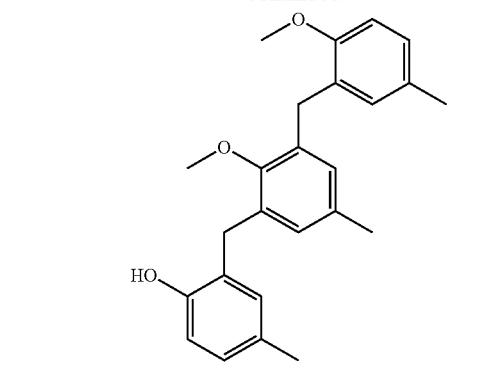
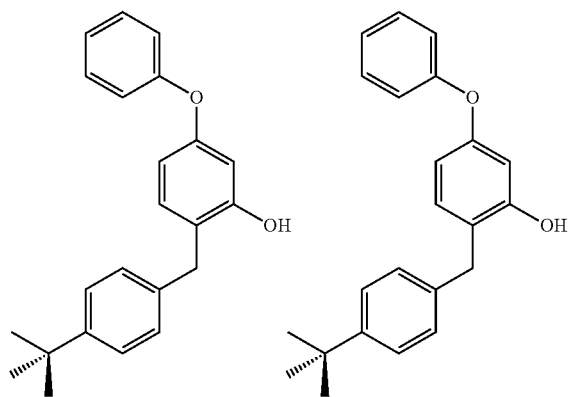
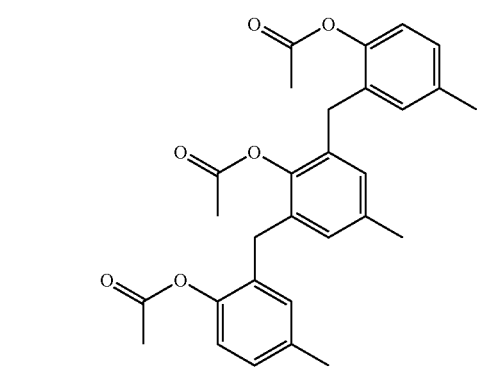
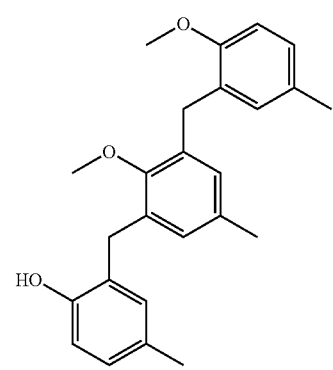
-continued
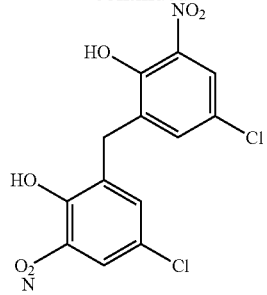
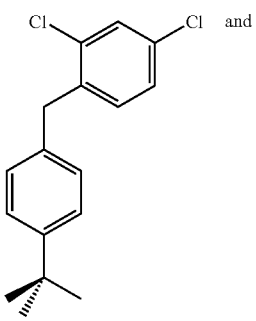
and
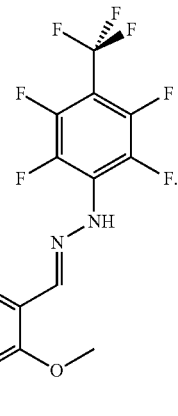
Most preferably, the compound of this group has an IC50 less than about 3 μM in cells overexpressing Bcl-$x_L$. Examples of such compounds include:
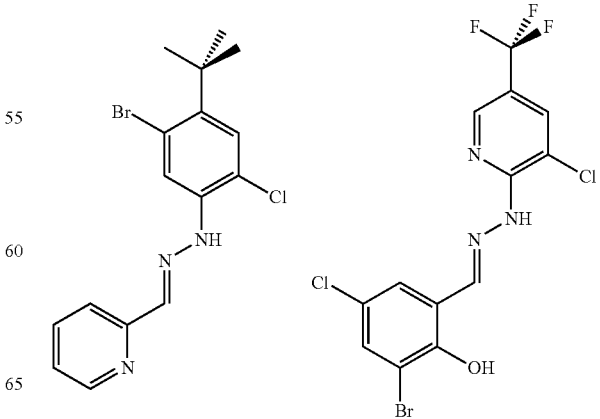

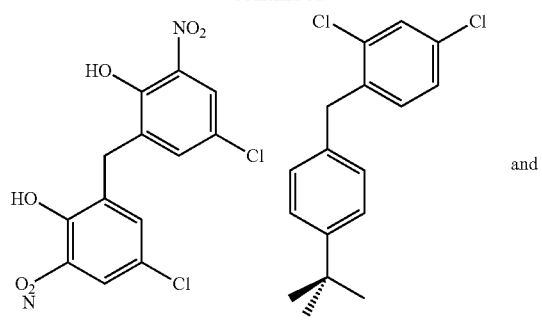

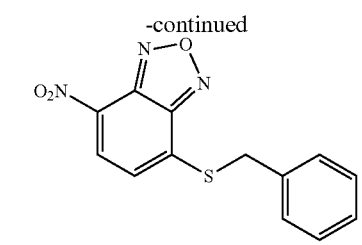

and

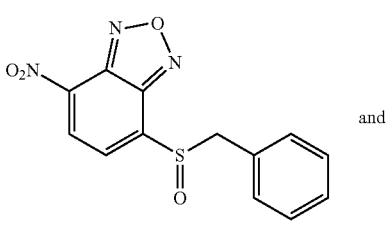

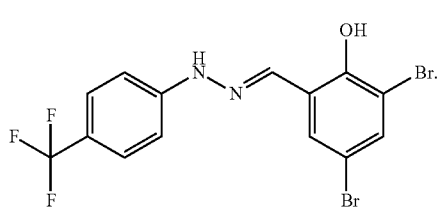

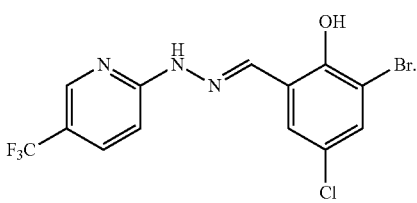

Another aspect of the invention is an active compound that has an IC50 less than about 3 micromole/liter (3 µM) in cells overexpressing Bcl-$x_L$, and at least about 3-fold less cytotoxic in isogenic cells that are not overexpressing Bcl-$x_L$. Examples of such compounds include:

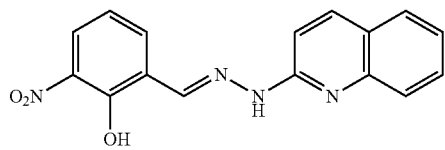

Most preferably, the active compound has an IC50 less than about 3 µM in cells overexpressing Bcl-$x_L$. Examples of such compounds include:

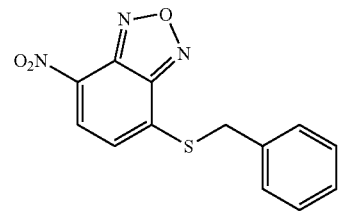

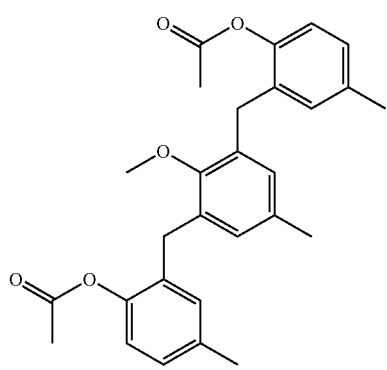

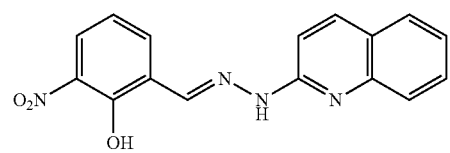

and

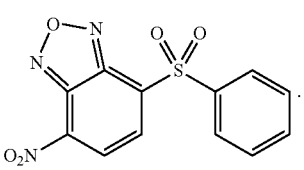

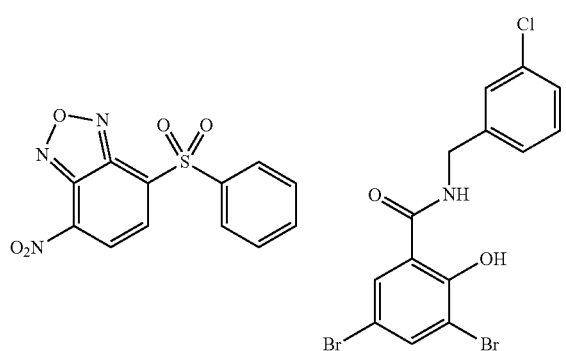

Another aspect of the invention is an active compound that has an IC50 less than about 5 micromole/liter (5 µM) in cells overexpressing Bcl-$x_L$, and at least about 2-fold less cytotoxic in isogenic cells that are not overexpressing Bcl-$x_L$. Examples of this group of compounds include:

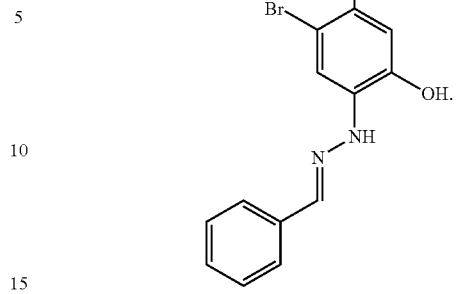

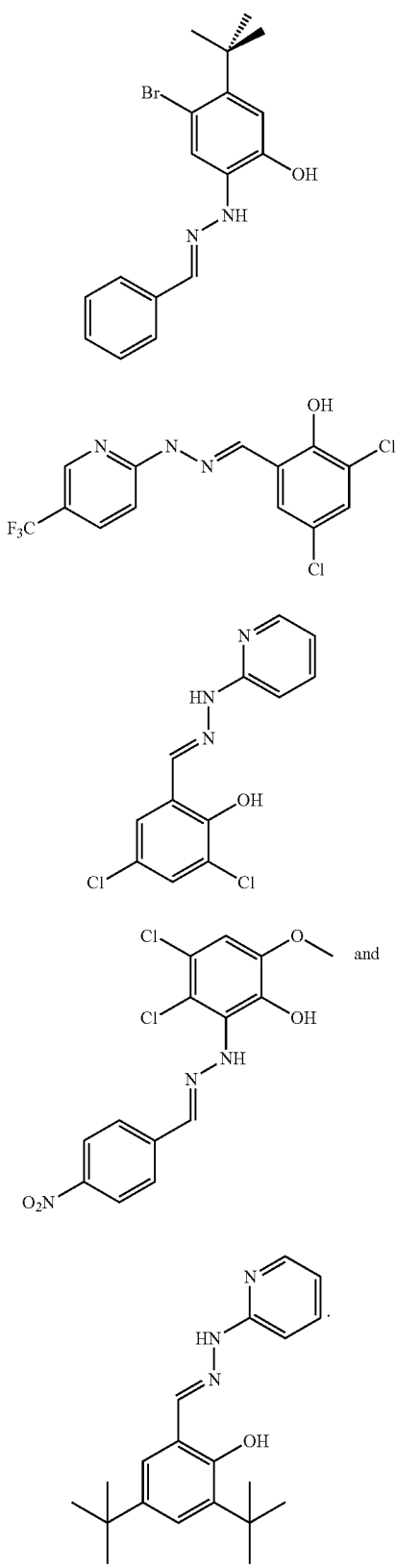

Most preferably, the active compound has an IC50 less than about 3 µM in cells overexpressing Bcl-x$_L$. An example of such compound is:

Another aspect of the invention is a method for treating an apoptosis-associated disease in a subject in need thereof, comprising administering to the subject a therapeutically effective amount of an active compound selected from any group of compounds described above.

Another aspect of the present invention resulted from an effort to create scaffolds of compounds and test them by screening for selective cytotoxicity in cells having a gain-of-function phenotype (i.e., elevated expression of a Bcl-2, anti-apoptotic family member) and minimal cytotoxicity in isogenic cells that are not overexpressing Bcl-2).

One aspect of the present invention is a method of treating an apoptosis-associated disease with the molecules resulting from this screening process.

One embodiment of the present invention is a method for treating an apoptosis-associated disease (e.g., cancer) in a subject in need thereof, comprising administering to the subject a therapeutically effective amount of an active compound as described herein, such as Formula I, as follows:

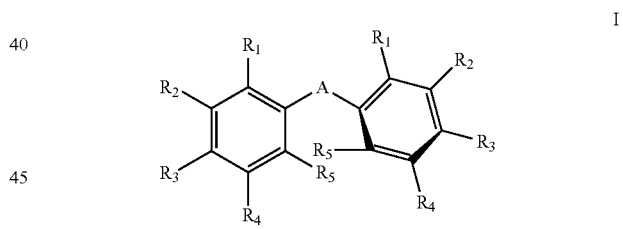

I wherein
A is S, CH$_2$, SO, SO$_2$, CO, O, NR, and COHPh;
R$_1$ is selected from the group consisting of hydroxyl and NO$_2$;
R$_2$ is H, hydroxyl, halide, or alkyl;
R$_3$ is H, alkyl, or aryl linked to R$_4$;
R$_4$ is H, halide, alkyl, or aryl linked to R$_3$; and
R$_5$ is H or alkyl.

Preferably, the method comprises administering Formula I compound, wherein:
R$_1$ is hydroxyl,
R$_2$ is H, halide, methyl or t-butyl;
R$_3$ is H or methyl;
R$_4$ is halide or methyl; or
R$_5$ is H, methyl or t-butyl.

More preferably, the method comprises administering Formula I, described as follows:
A is selected from the group consisting of S, CH$_2$, SO, and SO$_2$;

R₁ is hydroxyl;

R₂ is H, Cl, methyl or t-butyl;

R₃ is H or methyl;

R₄ is H, Cl, Br, or methyl; and

R₅ is H, methyl, or t-butyl.

Most preferably, the method comprises administering one or more particular embodiments of Formula I, selected from the following group:

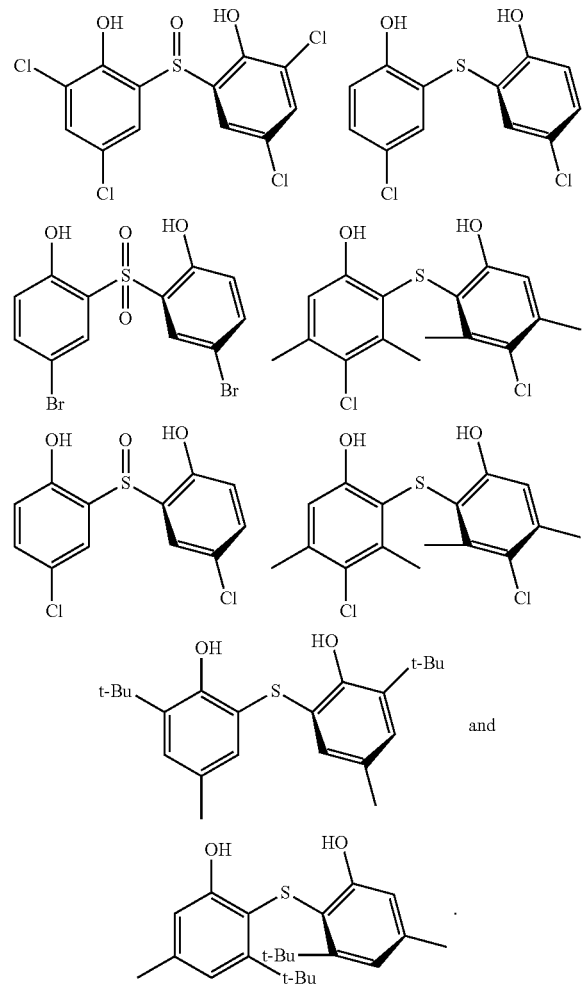

Preferably, the active compound of Formula I has an IC50 less than about 15 micromole/liter (15 μM) in cells overexpressing Bcl-x$_L$, and at least about 5-fold less cytotoxic in isogenic cells that are not overexpressing Bcl-x$_L$. Examples of active compounds of Formula I with this property are:

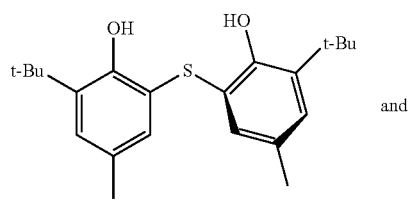

Most preferably, the active compound has an IC50 less than about 10 μM in cells overexpressing Bcl-x$_L$. Examples of Formula I compounds are:

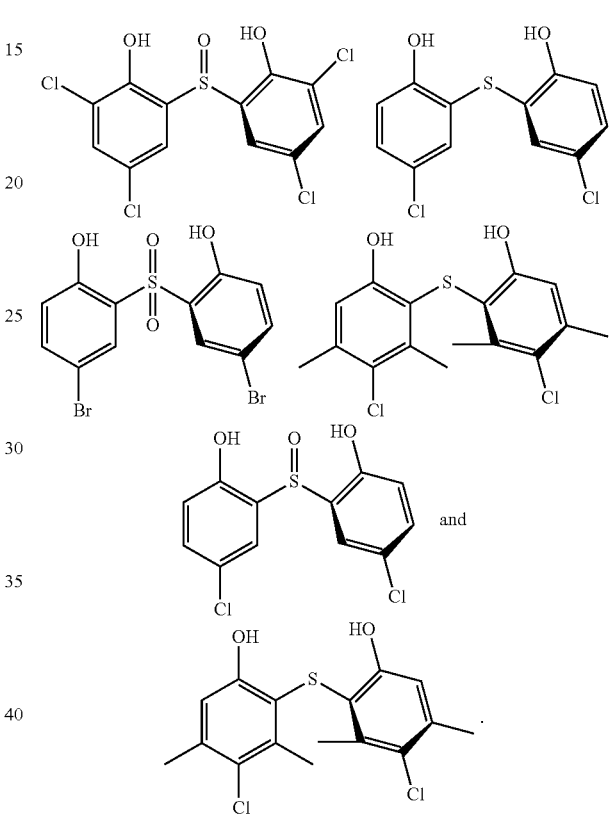

Another embodiment of the present invention is a method for treating an apoptosis-associated disease (e.g., cancer) in a subject in need thereof, comprising administering to the subject a therapeutically effective amount of an active compound as described herein, such as Formula II, a follows:

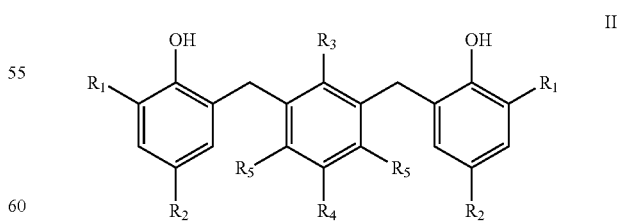

wherein

R₁ is hydroxyl or NO₂;

R₁ is H, alkyl, methyl halide, or COMe;

R₂ is alkyl or halide;

R₃ is H or hydroxyl;

$R_4$ is H, halide, COMe, or alkyl; and $R_5$ is H or alkyl.

Preferably, the method comprises administering Formula II, described as follows:

A and $A_2$ are each independently selected from the group consisting of H, alkyl, methyl halide, methyl alcohol, and COMe;

$R_2$ is alkyl or halide;

$R_3$ is H or hydroxyl;

$R_4$ is selected from the group consisting of H, halide, COMe, and alkyl; and $R_5$ is H or alkyl.

More preferably, the method comprises administering Formula II, described as follows:

$R_1$ is H, methyl, t-butyl, methyl chloride, methyl alcohol, or COMe;

$R_2$ is methyl, t-butyl, or Cl;

$R_3$ is hydroxyl;

$R_4$ is methyl, Cl, or t-butyl; and $R_5$ is H.

Most preferably, the method comprises administering at least one of the Formula II compounds.

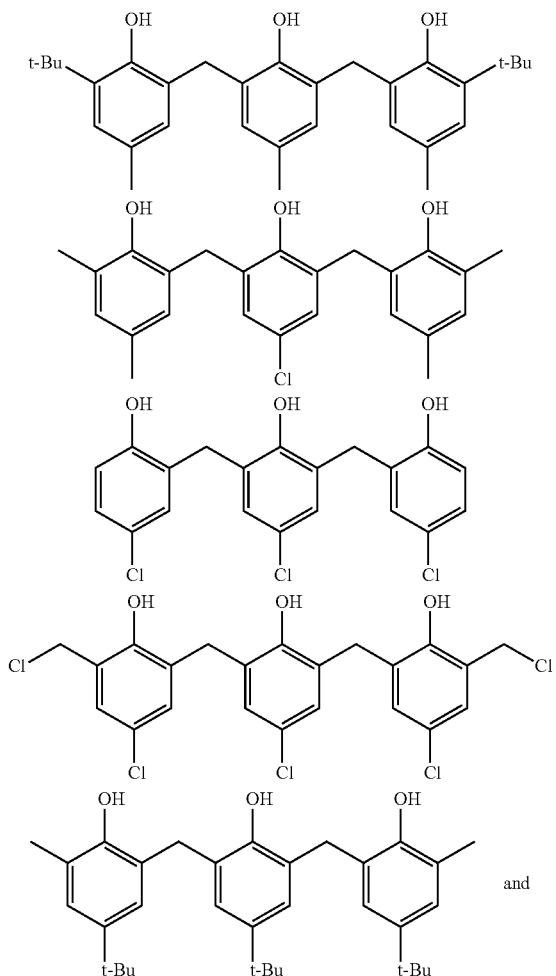

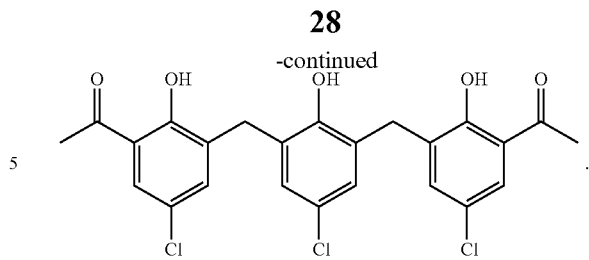

Preferably, the method comprises administering an active compound of Formula II that has an IC50 less than about 5 μM in cells overexpressing Bcl-$x_L$, and at least about 4-fold less cytotoxic in isogenic cells that are not overexpressing Bcl-$x_L$. Examples of such compounds are as follows:

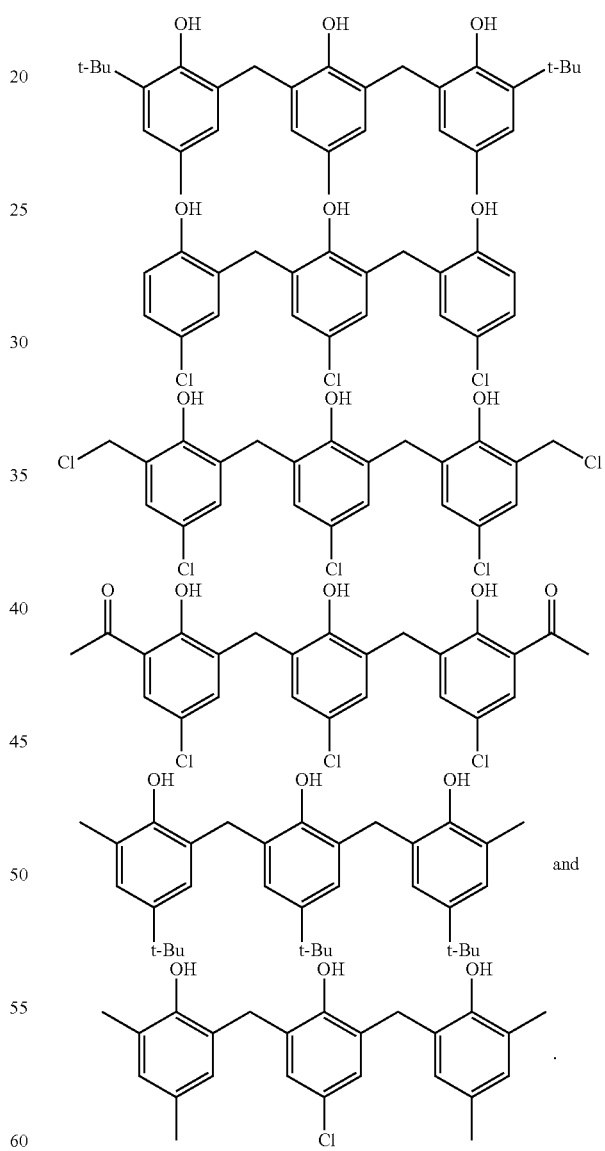

Another embodiment of the present invention is a method for treating an apoptosis-associated disease (e.g., cancer) in a subject in need thereof, comprising administering to the subject a therapeutically effective amount of an active compound as described herein, such as Formula III, a follows:

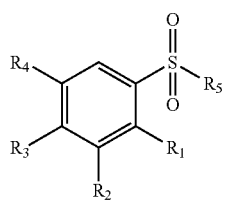

III wherein
- $R_1$ is hydroxyl, $NO_2$, or an oxadiazole formed with $R_2$;
- $R_2$ is H or an oxadiazole formed with $R_1$;
- $R_3$ is H, $NO_2$, or alkyl;
- $R_4$ is H or halogen; and
- $R_5$ is a substituted aryl or cycloalkyl group.

Preferably, the method comprises administering a Formula III compounds, wherein:
- $R_1$ is selected from the group consisting of hydroxyl, $NO_2$ and an oxadiazole formed with $R_2$;
- $R_2$ is H or an oxadiazole formed with $R_1$;
- $R_3$ is H, Cl, or $NO_2$.
- $R_5$ is 2-OH-5-Cl-Phenyl-, —CH$_2$-phenyl, 4-isopropyl-phenyl-, 2,4-dinitrophenyl-, and 2-chloro cyclohexane-.

Most preferably, the method comprises administering at least one of the Formula III compounds.

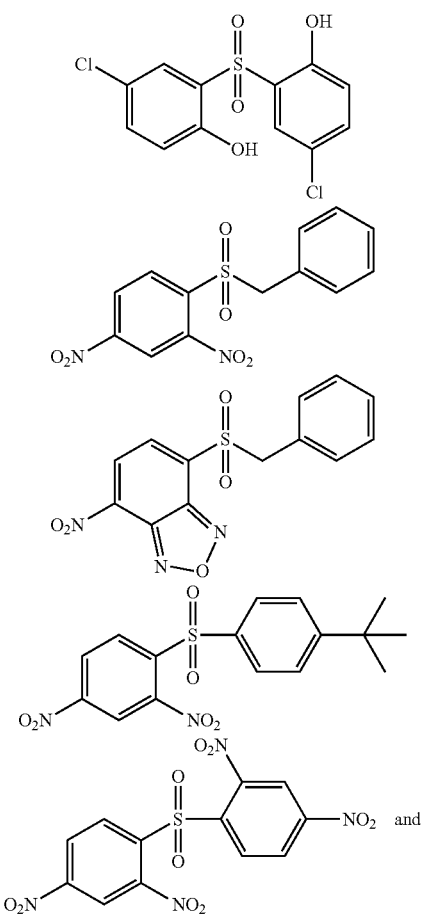

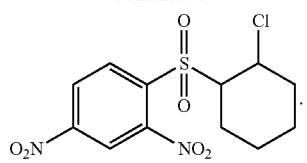

Preferably, the method comprises administering an active compound of Formula III has an IC50 less than about 15 μM in cells overexpressing Bcl-x$_L$, and at least about 2-fold less cytotoxic in isogenic cells that are not overexpressing Bcl-x$_L$. More preferably, the compound has at least about 3-fold less cytotoxic in isogenic cells that are not overexpressing Bcl-x$_L$. Examples of such compounds include the following structures:

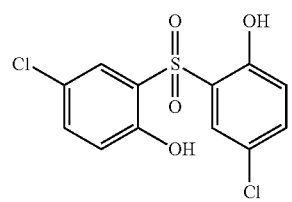

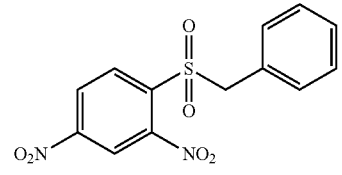

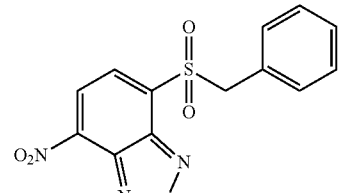

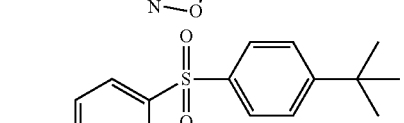

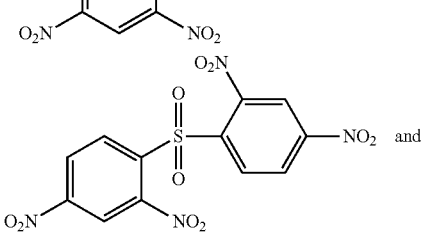

and

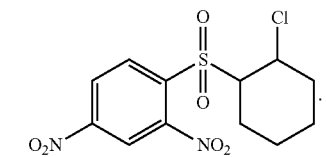

Another embodiment of the invention is a method for treating an apoptosis-associated disease in a subject in need thereof, comprising administering to the subject a therapeutically effective amount of an active compound of Formula IV:

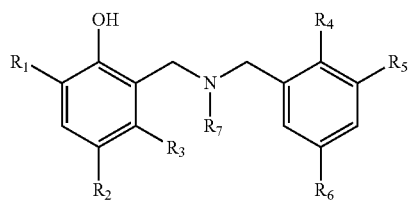

IV wherein $R_1$ and $R_5$ are each independently H, halide, or alkyl;

$R_2$ is alkyl, or phenyl with $R_3$;

$R_3$ is H, or phenyl with $R_2$;

$R_4$ is H or hydroxyl;

$R_6$ is H, halide, or alkyl; and $R_7$ is H, or alkyl.

Preferably, the method comprises administering a Formula IV compounds, wherein:

$R_1$ is H, Br, or methyl;

$R_2$ is methyl, t-butyl, or phenyl with $R_3$;

$R_3$ is H, or phenyl with $R_7$;

$R_5$ is H, Br, Cl, or methyl;

$R_6$ is H, Cl, Br, or t-butyl; and $R_7$ is H, methyl or ethyl.

Most preferably, the method comprises administering at least one of the Formula IV compounds:

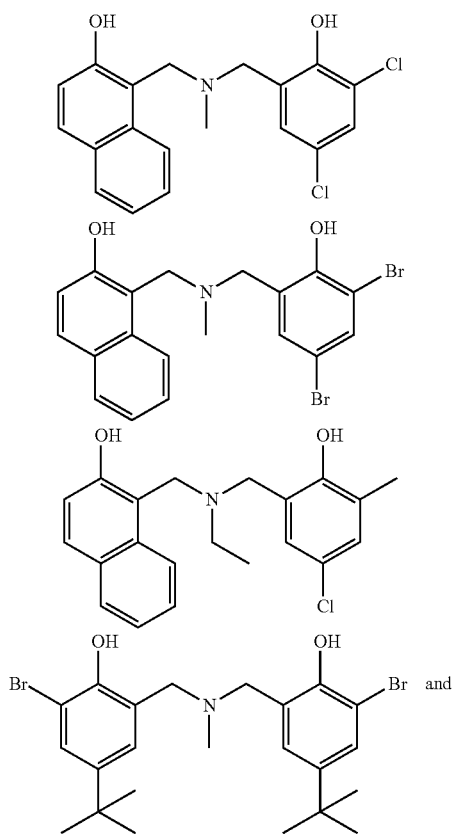

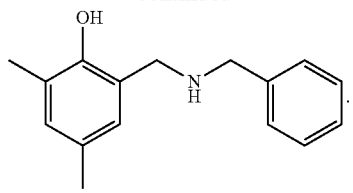

Preferably, the method comprises administering an active compound of Formula IV that has an IC50 less than about 10 micromole/liter (10 μM) in cells overexpressing Bcl-$x_L$, and at least about 8-fold less cytotoxic in isogenic cells that are not overexpressing Bcl-$x_L$. Examples of such compounds include the following structures:

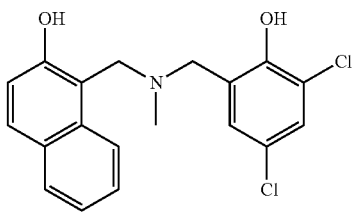

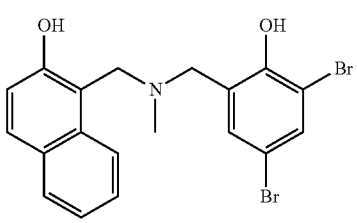

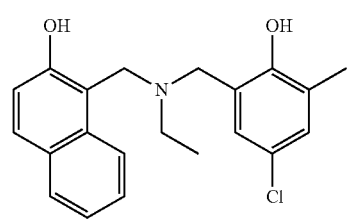

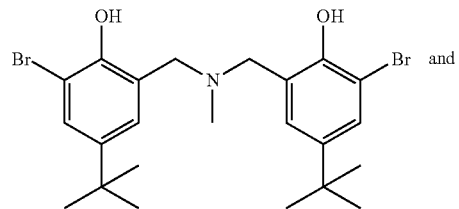

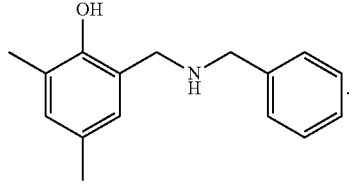

Another embodiment of the invention is a method for treating an apoptosis-associated disease in a subject in need thereof, comprising administering to the subject a therapeutically effective amount of an active compound of Formula V:

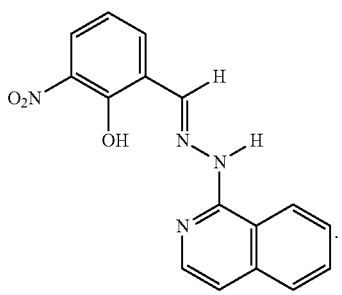 [SMILES: O=[N+]([O-])c1cccc(/C=N/Nc2nccc3ccccc23)c1O]

Another embodiment of the invention is a method for treating an apoptosis-associated disease in a subject in need thereof, comprising administering to the subject a therapeutically effective amount of an active compound of Formula VI:

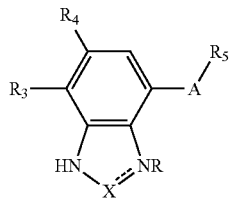

VI wherein
A is selected from the group consisting of S, $CH_2$, SO, $SO_2$, CO, O, NR, or COHPh;
$R_1$ is selected from the group consisting of hydroxyl and $NO_2$;
R2 is selected from the group consisting of H, alkyl, and aryl;
$R_3$ is selected from the group consisting of hydrogen, OH, $NO_2$, alkyl, and halogen;
$R_4$ is selected from the group consisting of halogen, and alkyl; and
$R_5$ is selected from the group consisting of H and alkyl.

Another embodiment of the present invention is a method for treating an apoptosis-associated disease (e.g., cancer) in a subject in need thereof, comprising administering to the subject a therapeutically effective amount of an active compound as described herein, such as Formula VII, a follows:

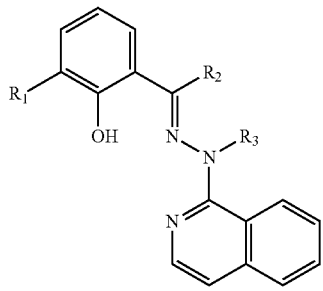

VII wherein:
$R_1$ is selected from the group consisting of H and $NO_2$;
$R_2$ is selected from the group consisting of Me and H; and
$R_3$ is selected from the group consisting of Me and H.

Another embodiment of the present invention is a method for treating an apoptosis-associated disease (e.g., cancer) in a subject in need thereof, comprising administering to the subject a therapeutically effective amount of an active compound as described herein, such as Formula VIII, a follows:

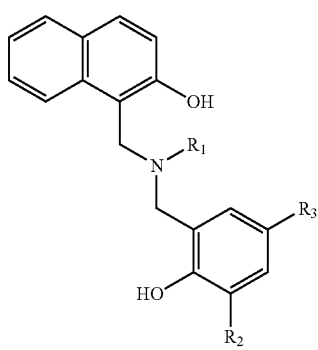

VIII wherein:
$R_1$ is selected from the group consisting of Me, Et, and cyhex;
$R_2$ is selected from the group consisting of Cl, Br, Me, and H; and
$R_3$ is selected from the group consisting of Cl, Br, Cl, and tBu.

Another embodiment of the present invention is a method for treating an apoptosis-associated disease (e.g., cancer) in a subject in need thereof, comprising administering to the subject a therapeutically effective amount of an active compound as described herein, such as Formula IX, as follows:

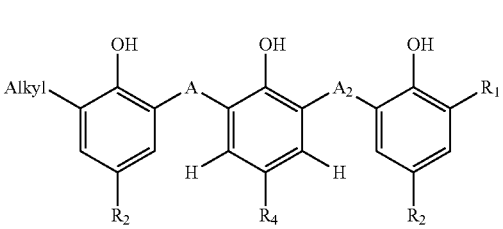

IX wherein:
A is S or SO;
$A_2$ is $CH_2$;
$R_1$ is selected from the group consisting of is alkyl, 5-aryl, SO-aryl, $SO_2$-aryl, and $CH_2$-aryl; and
$R_2$ and $R_4$ are each independently halogen or alkyl.

Embodiments of the present invention further provide a pharmaceutical formulation comprising, consisting of, or consisting essentially of an active compound of Formulae I through IX as described herein in combination with a pharmaceutically acceptable carrier.

Embodiments of the present invention provide a method of treating an apoptosis-associated disease (e.g., cancer) in a subject in need thereof, comprising administering to the subject a therapeutically effective amount of an active compound as described herein.

Embodiments of the present invention further provide the use of an active compound as described herein for the preparation of a medicament for treating an apoptosis-associated disease (e.g., cancer) in a subject in need thereof.

The foregoing and other objects and aspects of the present invention are explained in greater detail in the specification set forth below.

Methods of Using the Apoptosis-Modulating Compounds

The compounds of the present invention are useful for treating cells in which the cell death signal is down-regulated and the affected cell has an inappropriately diminished propensity for cell death, which is referred to herein as being in a "decreased apoptotic state." The invention further provides methods for the administration to a subject, a therapeutically effective amount of an apoptosis-modulating compound of the invention to treat an apoptosis-associated disease in which it is desirable to induce apoptosis in certain types of cells, such as virus-infected or autoantibody-expressing cells.

In a specific embodiment, a method of treating a cancer characterized by the over-expression of a Bcl-2 family member is provided. In some cases, the treatment of the cancer can include the treatment of solid tumors or the treatment of leukemias. For example, the cancer can be of the skin, breast, brain, cervix, testis, and the like. More particularly, cancers may include, but are not limited to, the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenal cortical carcinoma, kidney cancer, vascular cancer of various types, osteoblastic osteocarcoma, prostate cancer, ovarian cancer, uterine leiomyomas, salivary gland cancer, choroid plexus carcinoma, mammary cancer, pancreatic cancer, colon cancer, B and T cell lymphomas, acute and chronic myeloid or lymphoid leukemias, and multiple myeloma. Further, treatment may include pre-malignant conditions associated with any of the above cancers (e.g., colon adenomas, myelodysplastic syndrome). In other embodiments, methods of treating a neurodegenerative disease characterized by the over-expression of a Bcl-2 family member are provided. Neurodegenerative diseases include Alzheimer's disease, Parkinson's disease, amyotrophic lateral sclerosis, multiple sclerosis and other diseases linked to degeneration of the brain, such as Creutzfeldt-Jakob disease and expanded polyglutamine repeat diseases. Expanded polyglutamine repeat diseases with which the present invention is concerned include, but are not limited to, Huntington's disease, dentatorubral pallidoluysian atrophy, spinobulbar muscular atrophy, and spinocerebellar ataxia types 1, 2, 3, 6 and 7. See, e.g., Burke et al. U.S. Pat. No. 6,632,616.

In other embodiments, methods of treating arthritis, inflammation, autoimmune diseases, human immunodeficiency virus (HIV) immunodeficiency syndrome, myelodysplastic syndromes (such as aplastic anemia), ischaemic syndromes (such as myocardial infarction), liver diseases which are induced by toxins (such as alcohol), alopecia, damage to the skin due to UV light, lichen planus, atrophy of the skin, cataract, and graft rejections are provided. Typically, the compounds used in embodiments of the invention will be substantially purified prior to administration. The subject can be an animal, including, but not limited to, cows, pigs, horses, chickens, cats, dogs, and the like, and is typically a mammal, and in a particular embodiment human. In another specific embodiment, a non-human mammal is the subject. Various delivery systems are known and can be used to administer a compound of the invention, such as, for example, encapsulation in liposomes, microparticles, microcapsules, recombinant cells capable of producing the derivative, receptor-mediated endocytosis (see, e.g., Wu et al. J. Biol. Chem. 262: 4429-32, 1987), and the like. The apoptosis-modulating compounds are administered as therapeutic or pharmaceutical compositions by any suitable route known to the skilled artisan including, for example, intravenous, subcutaneous, intramuscular, intradermal, transdermal, intrathecal, intracerebral, intraperitoneal, intransal, epidural, and oral routes. Administration can be either rapid as by injection or over a period of time as by slow infusion or administration of slow release formulations. For treating tissues in the central nervous system, administration can be by injection or infusion into the cerebrospinal fluid (CSF). When it is intended that a compound be administered to cells in the central nervous system, administration can be with one or more other components capable of promoting penetration of the derivative across the blood-brain barrier. In addition, it can be desirable to introduce a compound into the target tissue by any suitable route, including intravenous and intrathecal injection. Pulmonary administration can also be employed, such as, for example, by use of an inhaler or nebulizer, and formulation of the compound with an aerosolizing agent. In certain embodiments, the compound is coadministered with an inhibitor of esterase activity to further stabilize the compound. Pharmaceutical compositions can also be administered orally in any orally acceptable dosage form including, but not limited to, capsules, tablets, caplets, lozenges, aqueous suspensions or solutions. In the case of tablets for oral use, carriers that are commonly used include lactose and corn starch. Lubricating aids, such as magnesium stearate, are also typically added. For oral administration in a capsule form, useful diluents include lactose and dried corn starch. When aqueous suspensions are required, the agent can be combined with emulsifying and suspending aids. If desired, certain sweeteners, flavorants, or colorants can also be used.

Further, the compounds of the present invention can be combined with any other tumor and/or cancer therapy. The therapy can include, for example and not by way of limitation, surgery, radiation, and chemotherapy either individually or in any combination. Chemotherapy can include any current known or yet to be discovered chemotherapeutic agent including but are not limited to Aceglatone; Aclarubicin; Altretamine; Aminoglutethimide; 5-Aminogleavulinic Acid; Amsacrine; Anastrozole; Ancitabine Hydrochloride; 17-1 A Antibody; Antilymphocyte Immunoglobulins; Antineoplaston AlO; Asparaginase; Pegaspargase; Azacitidine; Azathioprine; Batimastat; Benzoporphyrin Derivative; Bicalutamide; Bisantrene Hydrochloride; Bleomycin Sulphate; Brequinar Sodium; Broxuridine; Busulphan; Campath-1H; Caracemide; Carbetimer; Carboplatin; Carboquone; Carmofur; Carmustine; Chlorambucil; Chlorozotocin; Chromomycin; Cisplatin; Cladribine; *Corynebacterium parvum*; Cyclophosphamide; Cyclosporin; Cytarabine; Dacarbazine; Dactinomycin; Daunorubicin Hydrochloride; Decitabine; Diaziquone; Dichlorodiethylsulphide; Didemnin B.; Docetaxel; Doxifluridine; Doxorubicin Hychloride; Droloxifene; Echinomycin; Edatrexate; Elliptinium; Elmustine; Enloplatin; Enocitabine; Epirubicin Hydrochloride; Estramustine Sodium Phosphate; Etanidazole; Ethoglucid; Etoposide; Fadrozole Hydrochloride; Fazarabine; Fenretinide; Floxuridine; Fludarabine Phosphate; Fluorouracil; Flutamide; Formestane; Fotemustine; Gallium Nitrate; Gencitabine; Gusperimus; Homoharringtonine; Hydroxyurea; Idarubicin Hydrochloride; Ifosfamide; Ilmofosine; Improsulfan Tosylate; Inolimomab; Interleukin-2; Irinotecan; JM-216; Letrozole; Lithium Gamolenate; Lobaplatin; Lomustine; Lonidamine; Mafosfamide; Meiphalan; Menogaril; Mercaptopurine; Methotrexate; Methotrexate Sodium; Miboplatin; Miltefosine; Misonidazole; Mitobronitol; Mitoguazone Dihydrochloride; Mitolactol; Mitomycin; Mitotane; Mitozanetrone Hydrochloride; Mizoribine; Mopidamol; Muitlaichilpeptide; Muromonab-CD3; Mustine Hydrochloride; Mycophenolic Acid; Mycophenolate Mofetil; Nedaplatin; Nilutamide; Nimustine Hydrochloride; Oxaliplatin; Paclitaxel; PCNU; Penostatin; Peplomycin Sulphate; Pipobroman; Pirarubicin; Piritrexim Isethionate; Piroxantrone Hydrochloride; Plicamycin; porfimer Sodium; Prednimustine; Procarbazine Hydrochloride; Raltitrexed; Ranimustine; Razoxane; Rogletimide; Roquinimex; Sebriplatin; Semustine; Sirolimus; Sizofuran; Sobuzoxane; Sodium Bromebrate; Sparfosic Acid; Sparfosate Sodium; Sreptozocin; Sulofenur; Tacrolimus; Tamoxifen; Tegafur; Teloxantrone Hydrochloride; Temozolomide; Teniposide; Testolactone; Tetrasodium Mesotetraphenylporphine-sulphonate; Thioguanine; Thioinosine; Thiotepa; Topotecan; Toremifene; Treosulfan; Trimetrexate; Trofosfamide; Tumor Necrosis Factor; Ubenimex; Uramustine; Vinblastine Sulphate; Vincristine Sulphate; Vindesine Sulphate; Vinorelbine Tartrate; Vorozole; Zinostatin; Zolimomab Aritox; and Zorubicin Hydrochloride, and the like, either individually or in any combination. See, e.g., U.S. Pat. No. 7,071,158.

In some embodiments, the compounds of the present invention can be administered locally to the area in need of treatment; this administration can be achieved by, for example, and not by way of limitation, local infusion during surgery, topical application (e.g., in conjunction with a wound dressing after surgery), by injection, by means of a catheter, by means of a suppository, or by means of an implant, the implant being of a porous, non-porous, or gelatinous material, including membranes such as silastic membranes, or fibers. In one embodiment, administration can be by direct injection at the site (or former site) of a malignant tumor or neoplastic or pre-neoplastic tissue.

In another embodiment, the compounds of the invention can be delivered in a vesicle, in particular a liposome (see, e.g., Langer, Science 249:1527-33, 1990; Treat et al, In Liposomes in the Therapy of Infectious Disease and Cancer, Lopez-Berestein and Fidler (eds.), Liss, New York, pp. 353-65, 1989; Lopez-Berestein, supra, pp. 317-27).

In yet another embodiment, the compounds of the invention can be delivered in a controlled release system. In one embodiment, a pump can be used (see, e.g., Langer, supra; Sefton, CRC Crit. Ref. Biomed. Eng. 14:201, 1987; Buchwald et ah, Surgery 88:507, 1980; Saudek et al., N. Engl. J. Med. 321:574, 1989). In another embodiment, polymeric materials can be used (see, e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macro mol. Sci. Rev. Macromol. Chem. 23:61, 1983; see also Levy et al, Science 228:190, 1985; During et al, Ann. Neurol. 25:351, 1989; Howard et al, J. Neurosurg. 71:105, 1989). In yet another embodiment, a controlled release system can be placed in proximity of the therapeutic target, thus requiring only a fraction of the systemic dose (see, e.g., Goodson, Medical Applications of Controlled Release, supra, Vol. 2, pp. 115-138, 1984). Other controlled release systems are discussed in, for example, the review by Langer (Science 249: 1527-1533, 1990).

The present invention also provides pharmaceutical compositions. Such compositions comprise a pharmaceutically acceptable carrier and a therapeutically effective amount of a compound of the invention. The term "pharmaceutically acceptable" means approved by a regulatory agency of the Federal or a state government or listed in the U.S. Pharmacopeia or other generally recognized pharmacopeia for use in animals, and more typically in humans. The term "carrier" refers to a diluent, adjuvant, excipient, stabilizer, vehicle, or any combination thereof, with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired-can also contain minor amounts of wetting or emulsifying agents, or pH buffering agents. Pharmaceutical compositions can take the form of solutions, suspensions, emulsion, tablets, pills, capsules, powders, sustained-release formulations, and the like. The composition can be formulated as a suppository, with traditional binders and carriers such as triglycerides. In addition, in certain embodiments, the pharmaceutical composition includes an inhibitor of esterase activity as a stabilizing agent.

Oral formulations can include standard carriers such as pharmaceutical grades of mannitol, lactose, starch, magnesium stearate, sodium saccharine, cellulose, magnesium carbonate, and the like. Examples of suitable pharmaceutical carriers are described in, for example, Remington's Pharmaceutical Sciences, by E. W. Martin. Such compositions will contain a therapeutically effective amount of a compound of the invention, typically in purified form, together with a suitable amount of carrier so as to provide a formulation proper for administration to the subject. The formulation should suit the mode of administration.

In one embodiment, the compound of the present invention is formulated in accordance with routine procedures as a pharmaceutical composition adapted for intravenous administration to human beings. Typically, pharmaceutical compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form. For example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compounds of the invention can be formulated as neutral or salt forms. A "pharmaceutically acceptable salt" as used herein refers to a salt form of a compound permitting its use or formulation as a pharmaceutical and which retains the biological effectiveness of the free acid and base of the specified compound and that is not biologically or otherwise undesirable. Examples of such salts are described in *Handbook of Pharmaceutical Salts: Properties, Selection, and Use*, Wermuth, C. G. and Stahl, P. H. (eds.), Wiley-Verlag Helvetica Acta, Zurich, 2002. Examples of pharmaceutically acceptable salts, without limitation, include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine and the like. Examples of salts also include sulfates, pyrosulfates, bisulfates, sulfites, bisulfltes, phosphates, monohydrogenphosphates, dihydrogen phosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycolates, tartrates, methanesulfonates, ethane sulfonates, propanesulfonates, toluenesulfonates, naphthalene-1-sulfonates, naphthalene-2-sulfonates, and mandelates. In some embodiments, pharmaceutically acceptable salt includes sodium, potassium, calcium, ammonium, trialkylarylammonium and tetraalkylammonium salts.

Furthermore, "pharmaceutically acceptable prodrugs" of the compounds may be used in embodiments of the invention. Pharmaceutically acceptable prodrugs as used herein refers to those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formula, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design*, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The amount of the compound of the invention that is combined with the carrier to produce a single dosage form will vary, depending upon the nature of that agent and the composition of the dosage form. It should be understood, however, that a specific dosage and treatment regime for any particular patient or disease state will depend upon a variety of factors, including the age, body weight, general health, sex, diet, time of administration, rate of excretion, drug combination, the judgment of the treating physician, and the severity of the particular disease being treated. The amount of active agent will also depend upon the specific activity of the compound and whether that agent is co-administered with any other therapeutic or prophylactic ingredients. Determination of therapeutically effective dosages is typically based on animal model studies and is guided by determining effective dosages and administration protocols that significantly reduce the occurrence or severity of the apoptosis-associated disease in model subjects (e.g., in the case of treatment of malignancies, a tumor xenograft model in mice can be used. For treatment of human subjects, such animal model studies are typically followed up by human clinical trials. A non-limiting range for a therapeutically effective amount of the compounds is about 0.001 mg/kg and about 100 mg/kg body weight per day, and in more specific embodiments between about 0.00 mg/kg and about 50 mg/kg, between about 0.01 mg/kg and about 20 mg/kg. between about 0.1 and about 10 mg/kg, or between about 0.1 mg/kg and about 5 mg/kg body weight per day.

The invention also provides a pharmaceutical pack or kit comprising one or more containers filled with one or more of the ingredients of the pharmaceutical compositions of the invention. Optionally associated with such containers can be a notice, in the form prescribed by a governmental agency, regulating the manufacture, use, or sale of pharmaceuticals or biological products. The government notice should reflect approval by the agency of manufacture, use, or sale for human administration.

The following examples are provided merely as illustrative of various aspects of the invention and shall not be construed to limit the invention in any way.

EXAMPLES

Example 1

To examine the sensitivity of cells over-expressing Bcl-x$_L$ to various mitochondrial inhibitors and apoptosis inducers, cell lines over-expressing Bcl-x$_L$ were prepared and tested according to Hockenberry et al. U.S. Pat. No. 7,241,804, hereby incorporated by reference in its entirety. Competitive binding of compounds with fluorescent antimycin A$_3$, and competitive binding of compounds with BH3 peptide and Bcl-2. Competitive binding of compounds with BH-3 peptide were also measured using Bcl-x$_L$ as previously described. Id.

Cell lines were grown in RPMI 1640 medium (Gibco, Grand Island, N.Y.) supplemented with 5% fetal bovine serum (Hyclone, Logan, Utah). Also shown is the ratio of TAMH cells expressing Bcl-xL to those expressing A142L (WT:142L). The assay measures the potency of various compounds with respect to inducing apoptosis in these cells.

Example 2

The selectivity and EC50 for the following compounds was determined (in Example 3):

The structure of various substituents of the Formula I (below) are given in Table 1.

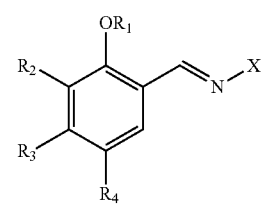

I wherein:

R$_1$ is H or alkyl;
R$_2$ is H, halide, or alkoxy;
R$_3$ is H, halide or alkyl;

$R_4$ is H, alkyl or alkoxy; and
X is —NH—$R_6$; —[C=O]—$R_6$; —NH—[C=O]—$R_6$—;
wherein $R_6$ is

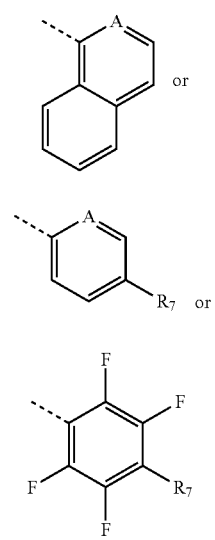

(i)

(ii)

(iii)

wherein

A is CH or N; and $R_7$ is H or $CF_3$.

TABLE 1

| H034 compound | A | X | $R_1$ | $R_2$ | $R_3$ | $R_4$ | $R_5$ | $R_6$ |
|---|---|---|---|---|---|---|---|---|
| 0239 | N | $NHR_6$ | H | Br | H | Cl | i | $CF_3$ |
| 0263 | CH | $NHR_6$ | Me | Br | H | Br | i | $CF_3$ |
| 0246 | CH | $NHR_6$ | H | Br | OMe | Br | ii | $CF_3$ |
| 0333 | CH | $NHR_6$ | H | OMe | H | Br | ii | $CF_3$ |
| 0298 | N | $COR_6$ | H | Br | H | Br | ii | $CF_3$ |
| 0347 | CH | $COR_6$ | H | Br | H | Br | ii | H |
| 0283 | CH | $NCOR_6$ | H | Br | H | OMe | ii | H |
| 0200 | N | $NHR_6$ | H | $NO_2$ | H | H | ii | Ph |
| 0235 | N | $NHR_6$ | H | Cl | H | Cl | ii | $CF_3$ |
| 0401 | N | $NHR_6$ | H | BR | H | tBu | ii | H |
| 0208 | N | $NHR_6$ | H | $NO_2$ | H | H | ii | H |
| 0351 | N | $NHR_6$ | H | H | OMe | Br | ii | H |
| 0355 | N | $NHR_6$ | H | Br | OMe | Cl | ii | H |
| 0241 | N | $NHR_6$ | H | H | H | Br | ii | H |
| 0231 | N | $NHR_6$ | H | H | H | Cl | ii | $CF_3$ |
| 0229 | N | $NHR_6$ | H | H | H | Cl | ii | H |
| 0245 | N | $NHR_6$ | H | Br | H | Br | ii | H |
| 0233 | N | $NHR_6$ | H | Cl | H | Cl | ii | H |
| 0353 | N | $NHR_6$ | H | H | tBu | Br | ii | H |
| 0275 | N | $NHR_6$ | H | Br | H | Cl | ii | $CF_3$ |
| 0240 | CH | $NHR_6$ | H | H | H | Br | ii | H |
| 0352 | CH | $NHR_6$ | H | H | tBu | Br | ii | H |
| 969 | CH | $NHR_6$ | Me | Br | H | Br | iii | $CF_3$ |
| 4636 | CH | $NHR_6$ | H | OMe | H | Cl | ii | $NO_2$ |
| 2476 | N | $NHR_6$ | H | H | OH | H | ii | $CF_3$ |
| 0725 | N | $NHR_6$ | OH | H | H | Br | ii | H |
| 0357 | CH | $NHR_6$ | H | tBu | H | tBu | ii | H |

The structure of various substituents of the Formula II and III (below) are given in Table 2.

TABLE 2

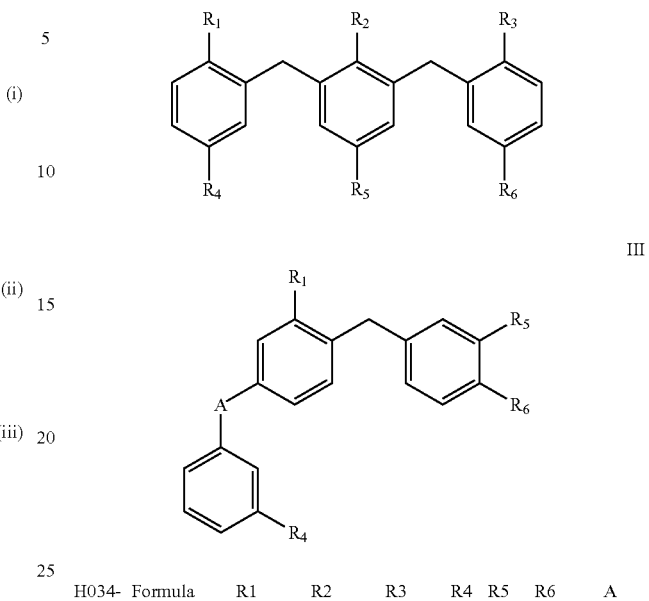

| H034- | Formula | R1 | R2 | R3 | R4 | R5 | R6 | A |
|---|---|---|---|---|---|---|---|---|
| 0039 | II | OH | OH | OH | Br | Me | Br | $CH_2$— |
| 0036 | II | OMe | OMe | OH | Me | Me | Me | $CH_2$ |
| 0088 | II | OMe | OMe | OH | Cl | Cl | Cl | $CH_2$ |
| 0098 | II | OAc | OAc | OAc | Me | Me | Me | $CH_2$ |
| 0051 | III | OH | — | — | Me | Me | H | $CH_2$ |
| 0155 | III | OH | — | — | H | H | t-Bu | O |
| 0151 | III | H | OH | H | H | H | t-Bu | — |
| 0125 | II | OAc | OMe | OAc | Me | Me | Me | $CH_2$ |
| 0127 | II | $OCOCMe_2$ | OH | $OCOCMe_2$ | Me | Me | Me | $CH_2$ |

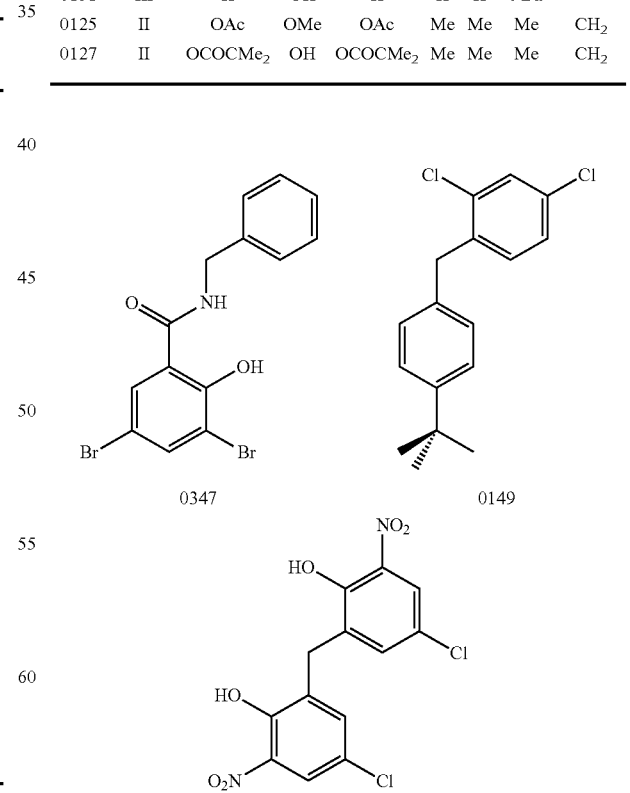

43

-continued

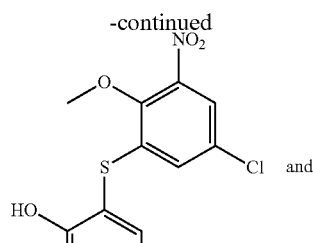

0083

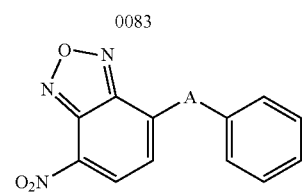

0216: A is —S—CH$_2$
0218: A is —SO—CH$_2$
0219: A is —SO$_2$—

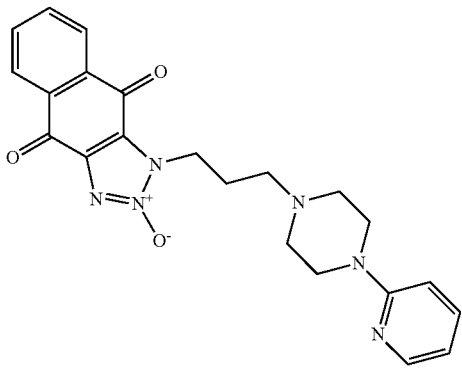

0511

Example 3

The compounds described in Example 2 were tested for their ability to inhibit Bcl-2 gain-of-function in TAMH cells, TAMH cells overexpressing Gclx$_L$ (TAMH-Bcl-x$_L$), TAMH cells transfected with Neo vector (Neo), TAMH cells overexpressing a variant of Bcl-x$_L$ (A142L) using the methods of Example 1. The results are shown in the following Tables. 3-6.

TABLE 3

| FC# | 2S EC50 | Neo EC50 | Log P |
|---|---|---|---|
| 0333 | 2.2 | 26.90 | 6.510 |
| 0298 | 2.3 | 13 | |
| 0283 | 2.5 | 50. | 3.730 |
| 0401 | 1.7 | 40.8 | 4.810 |
| 0355 | 1.6 | 33 | 3.820 |
| 0351 | 2.6 | 50 | 3.03 |
| 0241 | 0.2 | 50 | 2.740 |
| 0231 | 2.1 | 50 | 3.560 |
| 0229 | 2.4 | 50 | 2.570 |
| 0245 | 3.3 | 50 | 3.540 |
| 0233 | 3.5 | 50 | 3.190 |
| 0353 | 1.3 | 10 | 4.810 |
| 0275 | 1.4 | 9.9 | 4.980 |

44

TABLE 4

| Compound | Bcl-xL | Neo | Neo:Bcl | A142L | WT:142L |
|---|---|---|---|---|---|
| 0246 | 1.1 | 7.1 | 6.5 | 6.4 | 5.8 |
| 0200 | 1.9 | 7.4 | 3.9 | 4.1 | 2.2 |
| 0333 | 2.7 | >25 | 9.2 | 22.2 | 8.2 |
| 0263 | 2.9 | >25 | 10.6 | 10.7 | 3.7 |
| 0283 | 3.5 | >25 | 7.1 | >25 | 7.1 |
| 0235 | 3.9 | 11 | 2.8 | 8.5 | 2.2 |
| 0239 | 4.3 | 17.2 | 4 | 13.3 | 3.1 |
| 0401 | 4.4 | >25 | 5.7 | >25 | 2.2 |
| 0208 | 4.4 | >25 | 5.7 | 9.7 | 2.2 |
| 0351 | >25 | >25 | 1 | >25 | 1 |
| 2-MeAA1 | 2.5 | 15.6 | 6.9 | 10.3 | 4.1 |

TABLE 5

| H034 | 2S EC50 | Neo EC50 | Log P |
|---|---|---|---|
| 0039 | 0.7 | 2.9 | ND |
| 0036 | 1.9 | 17.5 | ND |
| 0088 | 0.6 | 6.1 | 7.4 |
| 0098 | 1.6 | 10.40 | 7.45 |
| 0051 | 1.5 | 15.40 | 6.18 |
| 0155 | 1.9 | 12 | 7.24 |
| 0127 | 3.2 | 50 | 8.31 |

TABLE 6

| H034 | 2S EC50 | Neo EC50 | Log P |
|---|---|---|---|
| 0347 | 00.5 | 5.8 | 4.250 |
| 0149 | 01.1 | 9.2 | 6.280 |
| 0151 | 0.6 | 2.5 | ND |
| 0219 | 7.6 | 50 | ND |
| 0216 | 1.2 | 3.7 | ND |

Example 4

The EC50 for the Compound 0216 (see structure above) was determined in a panel of pancreatic cell lines.

The panel included CFPAC-1, HPAF-II MIA PaCa, PaTu-1, PaTu-8988t, ASPC-1, FA-6, and PANC-1 cell lines. Pancreatic cancer samples were obtained from patients, with appropriate patient consent and approval of the Fred Hutchinson Cancer Research Center Institutional Review Board. Primary cells were maintained in Iscove's medium supplemented with 10% bovine calf serum, 100 ng·ml$^{-1}$ stem cell factor, and 50 ng·ml$^{-1}$ interleukin-3.

The EC50 values were measured with compound 216. FIG. 1 shows that the EC50 value for this molecule is less than 10 micromolar in every cell line, but for HPAF-II. This means that this molecule has a broad ability to induce apoptosis in a wide variety of pancreatic cancers.

Example 5

Compound 216 was tested in TAMH cells overexpressing Bcl-xL compared to TAMH cells transfected with the neo expression vector as in Example 2. The results (FIG. 2) show that compound cells overexpressing Bcl-xL are more sensitive to the apoptosis-inducing effects of compound 216. Without being bound to a mechanistic model for the mode of action of compound 216, these results suggest that heightened sensitivity to this compound is associated with levels of expression of the Bcl-xL gene.

To determine if expression levels of Bcl-xL correlated with sensitivity to the ability of compound 216 to induce apoptosis, relative expression levels of Bcl-2, Bcl-xL, and MCL-1 were measure in the pancreatic cell lines tested in Example 3. Levels of expression (FIG. 3) show that levels of Bcl-xL expression in HPAF-II cells are very low. This suggests that cells expressing Bcl-xL at lower levels are more refractory to the apoptotic inducing ability of compound 216.

Example 6

The ability of compounds from Example 2 to induce apoptosis against solid tumors in vitro was tested. Four solid tumors were tested: OVCAR-3, an ovarian tumor; COLO205, a colonic tumor; HOP-62 and H23, both NSCLC tumors. The experimental compounds were compared to 2MeAA and to ABT-737, a clinical stage compound owned by Abbott Pharma.

The results of measuring EC50, in micromolar units, are shown in Table 7.

TABLE 7

| Compound | OVCAR-3 | COLO205 | HOP-62 | H23 |
| --- | --- | --- | --- | --- |
| 2MeAA | 3.5 | 1.8 | 3.9 | 2.7 |
| ABT-737 | 17 | >25 | >25 | >25 |
| 0200 | 1.5 | 1.0 | 2.7 | 2.8 |
| 0235 | 2.7 | 6.7 | 8.3 | 3.7 |
| 0239 | 4.2 | >25 | 19.1 | 5.6 |
| 0208 | 3.8 | 9.2 | 17.5 | 8.2 |

The results show that the experimental compounds were effective in inducing apoptosis in a variety of solid tumors of different origin. The higher potency of these molecules suggests an increased efficacy in combination with chemotherapeutic agents in treating cancers. That is, being effective at concentrations having little or no toxicity is an advantage, particularly in combination therapy with chemotherapeutic agents.

Example 7

The ability of the experimental compounds to inhibit tumor growth in a body was tested in a mouse colon carcinoma xenograft model.

Six to nine-week old NOD/Les2 SCID/J mice were inoculated with $3\times10^7$ Colo205 cells by interscapular subcutaneous injection. Mice were maintained under specific pathogen-free conditions. Palpable tumor nodules were measured in two dimensions with calipers and tumor volumes calculated in mm3 as (length×width$^2$)/2. Blood samples were collected by retro-orbital bleed for human light chain measurements by ELISA using lambda-specific antibody (BD Biosciences). Animals were sacrificed by halothane inhalation, and histologic examination of the tumors and internal organs was performed. All experiments were approved by the FHCRC Institutional Animal Care and Use Committee.

Animals were treated by daily intraperitoneal administration of Compound 0511 (see structure above in Example 2). The results of this test (FIG. 4) show that administration of compound FH511 as a single agent is effective in inhibiting tumor growth.

Example 8

The selectivity and EC50 for the following compounds was determined (in Example 35):

Bis(2-hydroxy-5-chlorophenyl) sulfide (NSC 55636);

Bis-2,6-(2'-hydroxy-5'-chlorophenyl)-4-chlorophenol (NSC 47932);

4-(benzylsulfonyl)-7-(hydroxy(oxido)amino)-2,1,3-benzoxadiazole (NSC 228148);

2-hydroxy-3-(hydroxy(oxido)amino)benzaldehyde 2-quinolinylhydrazone (NSC 168468); and 2-((benzylamino)methyl)-4,6-dimethylphenol (NSC 47911).

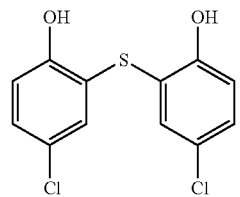

NSC 55636

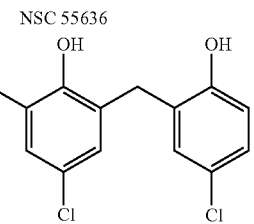

NSC 47932

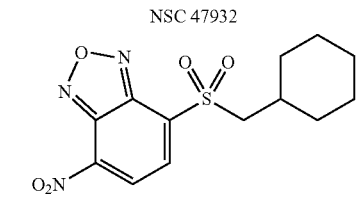

NSC 228148

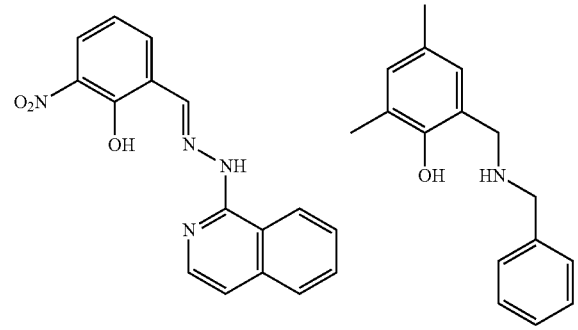

NSC 168468        NSC 47911

Example 9

The effects of the compounds described in Example 8 on TAMH cells, TAMH cells overexpressing Bcl-x$_L$ (TAMH-Bcl-x$_L$), TAMH cells transfected with Neo vector (Neo), TAMH cells over expressing a variant of Bcl-x$_L$ (A142L) is shown in Table 8

TABLE 8

| NSC ID # | TAMH Bcl-$x_L$ | TANH Neo | Neo/Bcl-$x_L$ | Competitive binding |
|---|---|---|---|---|
| 55636 | 1.9 | 14.7 | 7.7 | ++ |
| 47932 | 0.5 | 3.5 | 7 | ++ |
| 228148 | 6 | 22.5 | 3.8 | + |
| 168468 | 5.5 | NR | >15 | + |
| 47911 | 4.1 | 31.9 | 7.8 | + |

Competitive binding was also measured using purified Bcl-xL protein, and measuring the ability to compete with labeled 2-MeAA.

The results are show that these compounds are active in inducing apoptosis at low concentrations in cells that are overexpressing Bcl-xL. Further, these compounds are cytotoxic against lower expressing cells only at a much higher concentration, i.e., at a concentration more than 3-fold higher.

Example 10

The selectivity and EC50 for the following compounds was determined (in Example 5). The reference biphenyl structure indicates the positions of different substituents, which are detailed in Table 9, as follows:

TABLE 9

| NSC ID# | R1 | R2 | R3 | R4 | R5 | A |
|---|---|---|---|---|---|---|
| 13984 | OH | Phenyl | | H | H | COHPh |
| 55636 | OH | H | H | Cl | H | S |
| 67488 | OH | t-Butyl | H | Me | H | S |
| 106079 | OH | H | H | Br | H | $SO_2$ |
| 523910 | OH | Cl | H | Cl | H | SO |
| 9875 | OH | H | Me | Cl | Me | S |
| 24019 | OH | H | H | Cl | H | SO |
| 59685 | OH | H | Me | H | tBu | S |
| 52168 | OH | H | Me | Cl | Me | S |
| 330927 | OH | OH | H | Me | H | O |
| 47129 | OH | Cl | H | Cl | H | S |
| 406932 | OH | H | H | Cl | H | $SO_2$ |
| 5992 | OH | H | H | Phenyl | H | $CH_2$ |
| 77122 | OH | Me | H | Cl | H | $CH_2$ |
| 288938 | OH | t-Butyl | H | $CMe_2Ph$ | H | $CH_2$ |
| 9872 | OH | Cl | H | Cl | H | S |
| 85476 | OH | Me | H | H | H | $CH_2$ |
| 9874 | OH | Br | Me | Cl | Me | S |
| 5857 | OH | t-Butyl | H | Cl | Me | $CH_2$ |
| 7781 | OH | t-Butyl | H | Me | H | $CH_2$ |
| 1050 | OH | H | H | Br | H | $SO_2$ |
| 4112 | OH | H | H | Cl | H | S |
| 1049 | OH | H | H | Br | H | S |
| 4631 | OH | H | H | Br | H | CO |
| 7782 | OH | t-Butyl | H | Et | H | $CH_2$ |
| 39635 | OH | H | i-Propyl | H | H | S |
| 5992 | OH | Phenyl | | H | H | $CH_2$ |
| 11877 | OH | Phenyl | | H | H | S |
| 62419 | OH | CH2NMe2 | H | Cl | H | S |
| 143532 | OMe | H | Me | H | H | CO |
| 7215 | $NH_2$ | H | $NH_2$ | Me | H | $CH_2$ |
| 78834 | OMe | H | H | H | H | Ch2 |
| 59828 | OH | H | OH | H | H | S |
| 48684 | OH | $CO_2H$ | H | Cl | H | $CH_2$ |
| 39242 | OH | $CH_2NMe_2$ | H | Cl | H | $CH_2$ |

TABLE 9-continued

| NSC ID# | R1 | R2 | R3 | R4 | R5 | A |
|---|---|---|---|---|---|---|
| 2855 | OH | H | H | t-Butyl | H | S |
| 4581 | OH | H | NH(C=O)Me | H | H | S |

The identification number corresponds to the entry in the NCI database for published chemical compounds.

Example 11

The effects of the compounds described in Example 10 on TAMH cells, TAMH cells overexpressing Bcl-$x_L$ (TAMH-Bcl-$x_L$), TAMH cells transfected with Neo vector (Neo), TAMH cells over expressing a variant of Bcl-$x_L$ (A142L) is shown in the following Table 10

TABLE 10

| NSC ID # | IC50 TAMH Bcl-$X_L$ | IC50 TAMH Neo | Fold Select. (Neo/Bcl-$X_L$) | Comp. Binding |
|---|---|---|---|---|
| 13984 | 10.05 | NR | 10 | FL (+) |
| 55636 | 1.9 | 14.7 | 7.7 | ++ |
| 67488 | 14.6 | 100 | 6.8 | |
| 106079 | 5.4 | 35.4 | 6.5 | |
| 523910 | 2.2 | 14.2 | 6.4 | + |
| 9875 | 0.9 | 5.7 | 6.3 | |
| 24019 | 5.6 | 32.2 | 5.7 | |
| 59685 | 12 | 66.4 | 5.5 | |
| 52168 | 1 | 5.2 | 5.2 | |
| 330927 | 19.8 | 100 | 5 | + |
| 47129 | 0.5 | 2.3 | 4.6 | |
| 406932 | 13.6 | 57.2 | 4.4 | |
| 5992 | 3 | 12.2 | 4.1 | +/− |
| 77122 | 2 | 6.6 | 3.3 | |
| 288938 | 28 | 93.1 | 3.3 | |
| 9872 | 2.3 | 7.5 | 3.3 | + |
| 85476 | 18.8 | 55.3 | 2.9 | |
| 9874 | 0.7 | 2.0 | 2.8 | |
| 5857 | 4.5 | 12.5 | 2.8 | + |
| 7781 | 1.6 | 4.5 | 2.8 | +/− |
| 1050 | 3.8 | 10.5 | 2.8 | |
| 4112 | 2 | 4.7 | 2.3 | |
| 1049 | 1.9 | 4.2 | 2.2 | |
| 4631 | 8.5 | 14 | 1.7 | ++ |
| 7782 | 2.1 | 3.5 | 1.7 | |
| 39635 | 4.3 | 7.8 | 1.3 | |
| 5992 | 4.4 | 8.0 | 1.8 | |
| 11877 | 54.8 | 100 | 1.8 | |
| 62419 | 20 | 36.1 | 1.8 | |

Competitive binding was also measured using purified Bcl-xL protein, and measuring the ability to compete with labeled 2-MeAA.

The results show that these compounds are active in inducing apoptosis at low concentrations in cells that are overexpressing Bcl-xL. Only at much higher concentrations were the compounds cytotoxic against lower expressing cells.

The 2-OH phenyl is the most active pharmacophore. The S, SO and CH2 bridges showed good selectivity.

A number of diphenyl compounds were inactive. These are listed in Table 11:

TABLE 11

| NSC ID# | IC50 TAMH Bcl-$X_L$ | IC50 TAMH Neo | Fold Select. (Neo/Bcl-$X_L$) | Comp. Binding |
|---|---|---|---|---|
| 143532 | NR | NR | 0 | |
| 7215 | NR | NR | 0 | ND |
| 78834 | NR | NR | 0 | |
| 59828 | NR | NR | 0 | |
| 48684 | NR | NR | 0 | — |
| 39242 | NR | NR | 0 | |
| 2855 | NR | NR | 0 | |
| 4581 | NR | NR | 0 | |

Generally, the 2-H, —OMe, and —NH2 diphenyl structures are inactive compounds in this series.

Example 12

The selectivity and EC50 for the following compounds was determined (in Example 13). The reference triphenyl structure indicates the positions of different substituents, which are detailed in Table 12 as follows:

TABLE 12

| NSC ID# | R1 | R2 | R3 | R4 | R5 |
|---|---|---|---|---|---|
| 62914 | t-Butyl | Me | OH | Me | H |
| 48444 | CH$_2$Cl | Cl | OH | Cl | H |
| 48698 | COMe | Cl | OH | Cl | H |
| 47932 | H | Cl | OH | Cl | H |
| 634604 | Me | t-Butyl | OH | t-Butyl | H |
| 48167 | Me | Me | OH | Cl | H |
| 48445 | CH$_2$OH | Cl | OH | Cl | H |
| 48168 | Me | Me | OH | H | H |
| 48705 | Me | Me | OH | COMe | H |
| 57725 | t-Butyl | Me | H | H | Me |

Example 13

The effects of the triphenyl compounds described in Example 12 on TAMH cells, TAMH cells overexpressing GclxL (TAMH-Bcl-xL), TAMH cells transfected with Neo vector (Neo), TAMH cells over expressing a variant of Bcl-xL (A142L) is shown in the following Table 13.

TABLE 13

| NSC ID# | IC50 TAMH Bcl-$x_L$ | IC50 TAMH Neo | Fold Select. (Neo/Bcl-$x_L$) | Comp. Binding |
|---|---|---|---|---|
| 62914 | 4.8, 1.1 | NR, 25 | >20, 22.7 | + |
| 48444 | 1.3 | 12.1 | 9.3 | |
| 48698 | 0.7 | 5.7 | 8.1 | |
| 47932 | 0.5 | 3.5 | 7 | ++ |
| 634604 | 5.0 | 32.1 | 6.4 | |
| 48167 | 1.4 | 5.6 | 4 | |
| 48445 | 1.8 | 4.5 | 2.5 | |
| 48168 | NR | NR | 0 | |
| 48705 | NR | NR | 0 | |
| 57725 | NR | NR | -0 | |

Generally, the diphenyl compounds appear to be more selective and more potent than the diphenyl compounds.

Example 14

The selectivity and EC50 for the following compounds was determined. The reference sulfoxyl structure indicates the positions of different substituents, which are detailed in Table 14, as follows:

TABLE 14

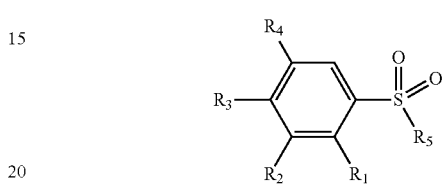

| NSC ID# | R1 | R2 | R3 | R4 | R5 |
|---|---|---|---|---|---|
| 406932 | OH | H | H | Cl | 2-OH-5-Cl—Ph |
| 122657 | NO$_2$ | H | NO$_2$ | H | CH$_2$—Ph |
| 228148 | Oxadiazole | | NO$_2$ | | CH$_2$—Ph |
| 85653 | NO$_2$ | H | NO$_2$ | H | 4-i-propyl-Ph |
| 122653 | NO$_2$ | H | NO$_2$ | H | 2,4-diNO$_2$—Ph |
| 405645 | NO$_2$ | H | NO$_2$ | H | 2-Cl-cyclohexane |
| 119944 | NO$_2$ | H | —CMe$_2$—CH$_2$-t-butyl | H | 2-OH-5-CMe$_2$—CH$_2$-t-butyl-Ph |

The effects of the sulfoxyl compounds described above on TAMH cells, TAMH cells overexpressing Bcl-$x_L$ (TAMH-Bcl-$x_L$), TAMH cells transfected with Neo vector (Neo), is shown in the following Table 15.

TABLE 15

| NSC ID# | IC50 TAMH Bcl-$X_L$ | IC50 TAMH Neo | Fold Selectivity (Neo/Bcl-$X_L$) | Comp. Binding |
|---|---|---|---|---|
| 406932 | 13.6 | 57.2 | 4.4 | + |
| 122657 | 3.5 | 13.5 | 3.9 | + |
| 228148 | 6 | 22.5 | 3.8 | + |
| 85653 | 4.5 | 12 | 2.7 | + |
| 122653 | 3.3 | 8.8 | 2.7 | + |
| 405645 | 2.9 | 6.1 | 2.1 | + |
| 119944 | 1.8 | 2.2 | 1.2 | |

Example 15

The selectivity and EC50 for the following hydrazide compound, 4-methoxy-N'-(3,3,6,8-tetramethyl-1-oxo-3,4-dihydro-2(1H)-naphthalenylidene)-benzohydrazide (NSC 310343), is show in following Table 16.

TABLE 16

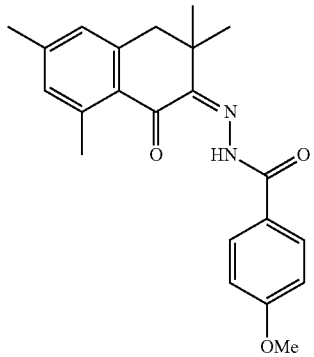 [SMILES: COc1ccc(C(=O)N/N=C2\C(=O)c3c(C)cc(C)cc3CC2(C)C)cc1]

| NSC ID# | TAMH Bcl-$X_L$ IC50 | TAMH Neo IC50 | Fold Selectivity (Neo/Bcl-$X_L$) | Comp. Binding |
|---|---|---|---|---|
| 310343 | 25 | NR | >4 | + |

Example 16

The selectivity and EC50 for the following hydrazone compounds is shown in the following Table 17, based on the common structural formula:

TABLE 17

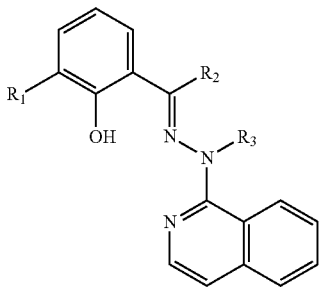

| ID# | R1 | R2 | R3 | Bcl-$x_L$ | Neo | Neo/Bcl-$x_L$ | Comp. Binding |
|---|---|---|---|---|---|---|---|
| 168466 | H | Me | H | NR | NR | — | NA |
| 168467 | H | H | Me | NR | NR | — | NA |
| 168468 | NO2 | H | H | 5.5 | NR | >15 | + |

Example 17

The selectivity and EC50 for the following naphthyl amine compounds is show in the following Table 18, based on the common structural formula:

TABLE 18

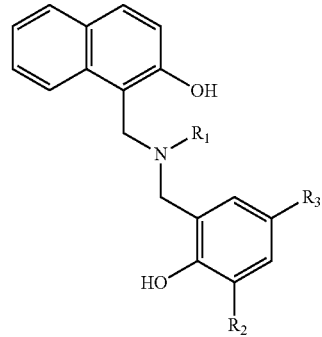

| ID# | R1 | R2 | R3 | Bcl-$X_L$ | Neo | Neo/Bcl-$X_L$ | Comp. Binding |
|---|---|---|---|---|---|---|---|
| 85479 | Me | Cl | Cl | 2.5 | 14.5 | 5.8 | — |
| 88852 | Me | Br | Br | 3.7 | 21.5 | 5.8 | — |
| 88850 | Et | Me | Cl | 4.5 | 12 | 2.7 | — |
| 48858 | Cyhex | H | t-Bu | NR | NR | — | NA |

Example 18

The selectivity and EC50 for the following benzyl amine compounds is show in the following Table 19, based on the common structural formula:

TABLE 19

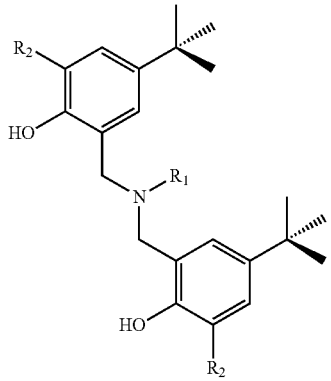

| ID# | R1 | R2 | Bcl-$X_L$ | Neo | Neo/Bcl-$X_L$ | Comp. Binding |
|---|---|---|---|---|---|---|
| 48881 | Me | Br | 6.1 | 28 | 4.6 | — |
| 48708 | Ph | H | NR | NR | — | NA |
| 48151 | Cyhex | H | NR | NR | — | NA |
| 48171 | Cyhex | Br | NR | NR | — | NA |

Example 19

The selectivity and EC50 for the following benzyl amine compound (NSC 47911) is show in the following Table 20:

TABLE 20

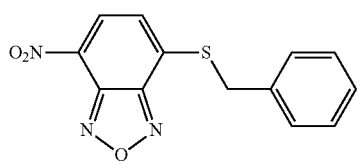

| ID# | Bcl-$X_L$ | Neo | Neo/Bcl-$X_L$ | Comp. Binding |
|---|---|---|---|---|
| 47911 | 4.1 | 31.9 | 7.8 | + |

Example 20

The EC50 for the compound FH279 (shown below) was determined in a panel of pancreatic cell lines.

FH279

The panel included CFPAC-1, HPAF-II MIA PaCa, PaTu-1, PaTu-8988t, ASPC-1, FA-6, and PANC-1 cell lines. Pancreatic cancer samples were obtained from patients, with appropriate patient consent and institutional approval. Primary cells were maintained in Iscove's medium supplemented with 10% bovine calf serum, 100 ng·ml$^{-1}$ stem cell factor, and 50 ng·ml$^{-1}$ interleukin-3.

The EC50 values were measured with compound FH279. FIG. 1 shows the results of this measurement, with EC50 values given in micromolar amounts.

The results of FIG. 1 show that the EC50 value for this molecule is less than 10 micromolar in every cell line, but for HPAF-II. This means that this molecule has a broad ability to induce apoptosis in a wide variety of pancreatic cancers.

Example 21

Figure 2:
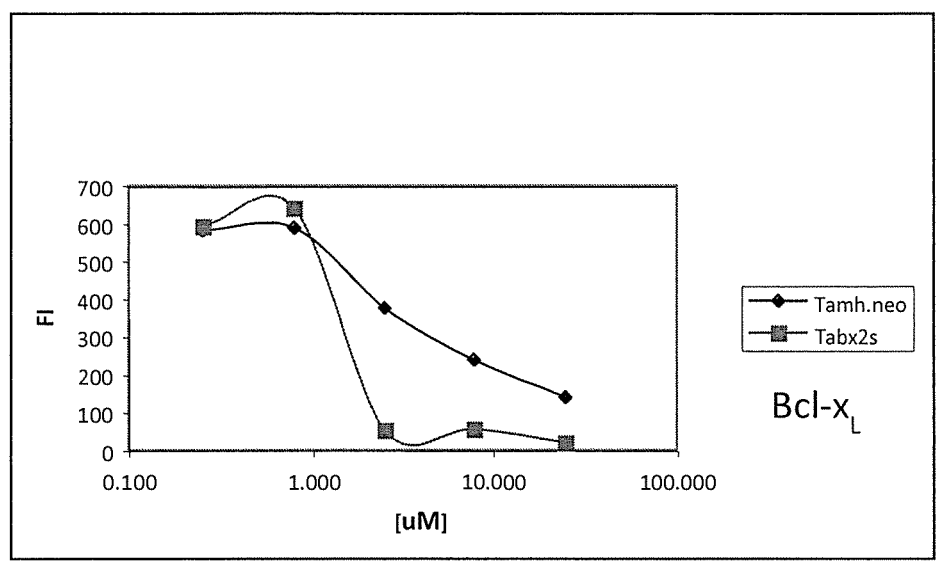
FIG. 2 shows the cytotoxic effect of FH279 (in micromolar units) on TAMH cells overexpressing Bcl-$x_L$ (Tabx2s, squares)) compared to TAMH cells transfected with a neo expression vector (Tamh.neo, circles), as described in Examples 5 and 21.

Compound FH279 was tested in TAMH cells overexpressing Bcl-$x_L$ compared to TAMH cells transfected with a neo expression vector. The results shown in FIG. 2 show that compound cells overexpressing Bcl-$x_L$ are more sensitive to the apoptosis-inducing effects of FH279. Without being bound to a mechanistic model for the mode of action of FH279, these results suggest that heightened sensitivity to this compound is associated with levels of expression of the Bcl-$x_L$ gene.

To determine if expression levels of Bcl-xL correlated with sensitivity to the ability of compound FH279 to induce apoptosis, relative expression levels of Bcl-2, Bcl-$x_L$, and MCL-1 were measure in pancreatic cell lines.

Figure 3A:
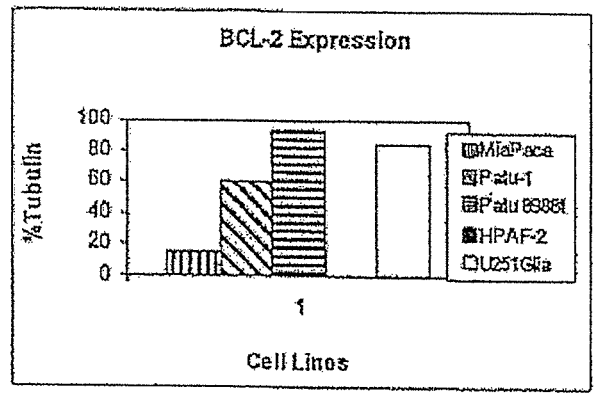
FIG. 3 shows the relative expression levels of Bcl-2 (FIG. 3A), Bcl-$x_L$ (FIG. 3B), and MCL-1 (FIG. 3C) measured in five pancreatic cell lines, expressed as percentage of control, maximal values, as described in Example 5 and 21.
Figure 3B:
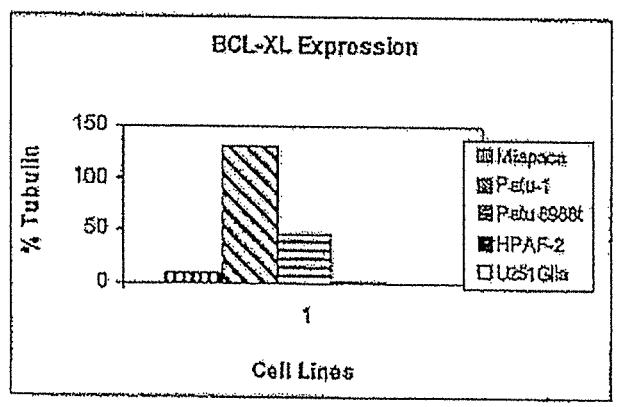
Figure 3C:
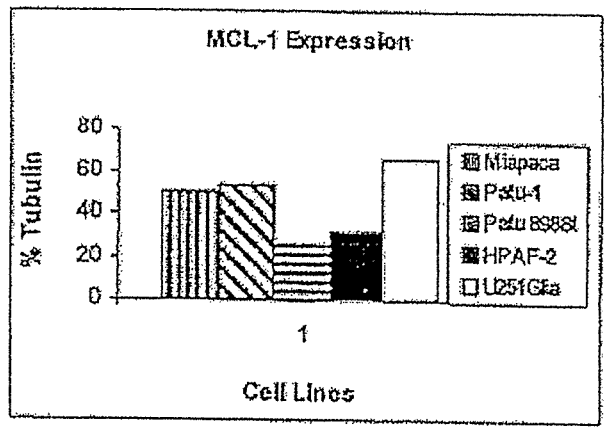

The results show that levels of Bcl-xL expression in HPAF-II cells was very low (FIGS. 3A, 3B and 3C). This suggests that cells expressing Bcl-xL at lower levels are more refractory to the apoptotic inducing ability of compound FH279.

Example 22

The ability of compounds of Example 8 to induce apoptosis against solid tumors in vitro was tested. Four solid tumors were tested: OVCAR-3, an ovarian tumor; COLO205, a colonic tumor; HOP-62 and H23, both NSCLC tumors. The experimental compounds,

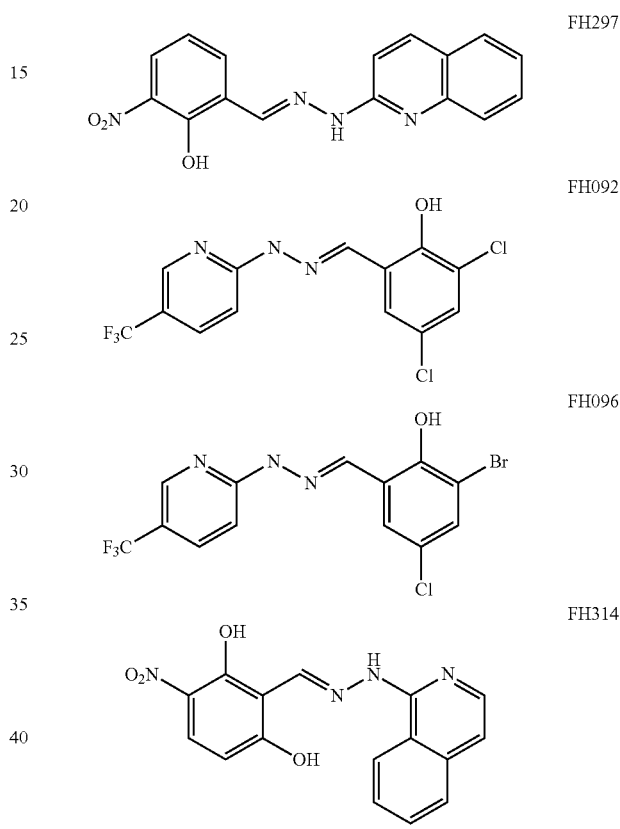

were compared to 2MeAA and to ABT-737, a clinical stage compound being developed by Abbott Pharma.

The results of measuring EC50, in micromolar units, are shown in Table 21.

TABLE 21

| Compound | OVCAR-3 | COLO205 | HOP-62 | H23 |
|---|---|---|---|---|
| 2MeAA | 3.5 | 1.8 | 3.9 | 2.7 |
| ABT-737 | 17 | >25 | >25 | >25 |
| FH297 | 1.5 | 1.0 | 2.7 | 2.8 |
| FH092 | 2.7 | 6.7 | 8.3 | 3.7 |
| FH096 | 4.2 | >25 | 19.1 | 5.6 |
| FH314 | 3.8 | 9.2 | 17.5 | 8.2 |

The results show that the experimental compounds were effective in inducing apoptosis in a variety of solid tumors of different origin. The higher potency of these molecules suggests an increased efficacy in combination with chemotherapeutic agents in treating cancers. That is, being effective at concentrations having little or no toxicity is an advantage, particularly in combination therapy with chemotherapeutic agents.

Example 23

The ability of the experimental compounds to inhibit tumor growth in a body was tested in a mouse colon carcinoma xenograft model.

Six to nine-week old NOD/Les2 SCID/J mice were inoculated with $3\times10^7$ Colo205 cells by interscapular subcutaneous injection. Mice were maintained under specific pathogen-free conditions. Palpable tumor nodules were measured in two dimensions with calipers and tumor volumes calculated in mm3 as (length×width$^2$)/2. Blood samples were collected by retro-orbital bleed for human light chain measurements by ELISA using lambda-specific antibody (BD Biosciences). Animals were sacrificed by halothane inhalation, and histologic examination of tumors and internal organs was performed. All experiments were approved by the FHCRC Institutional Animal Care and Use Committee.

Animals were treated by daily intraperitoneal administration of compound FH511, which has the following structure:

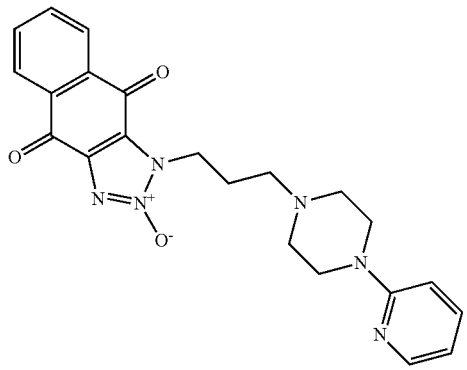 [SMILES: O=C1c2ccccc2C(=O)c2c1n[n+]([O-])n2CCCN1CCN(c2ccccn2)CC1]

Figure 4:
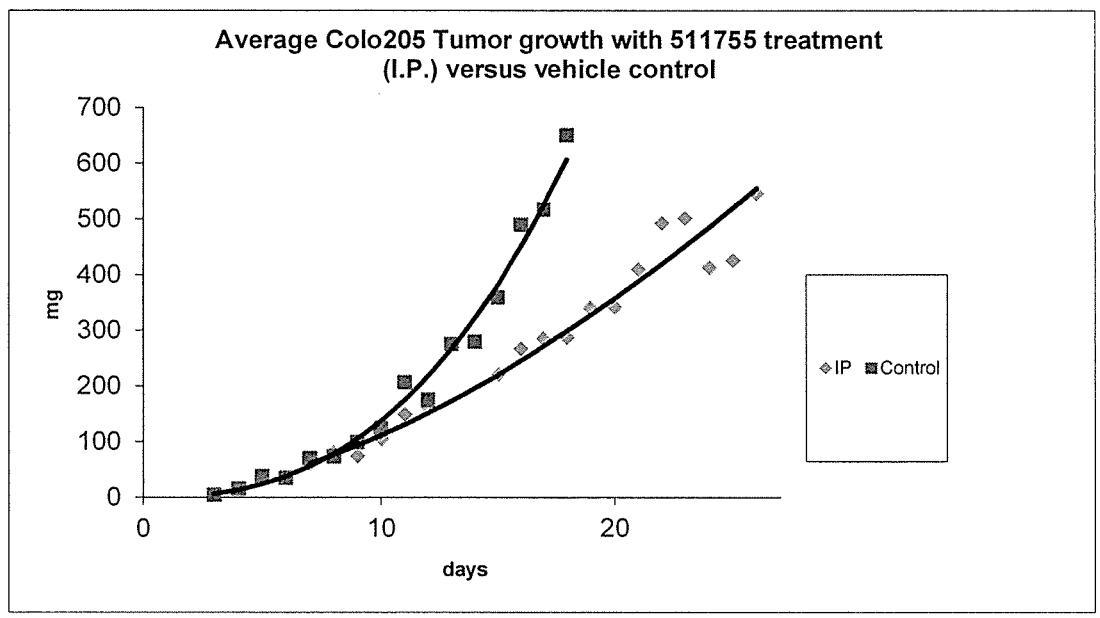
FIG. 4 shows the average tumor growth in an animal model following treatment with FH611 versus a vehicle control, as described in Examples 7 and 23.

The results of this test are described in FIG. 4.

The results show that administration of compound FH511 as a single agent is effective in inhibiting tumor growth.

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents. All publications and patent documents cited in this application are incorporated by reference in their entirety for all purposes to the same extent as if each individual publication or patent document were so individually denoted.

What is claimed:

1. An isolated compound consisting of Formula I

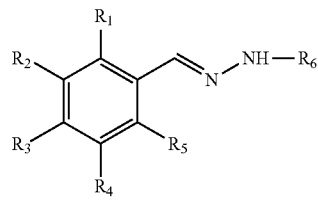

wherein:
  $R_1$ is OH, Cl, or methoxy;
  $R_2$ is NO$_2$, t-butyl or methoxy;
  $R_3$ is H, methyl, or t-butyl;
  $R_4$ is H, Cl, Br, t-butyl, or methyl
  $R_5$ is H, Cl, or OH; and
  $R_6$ is

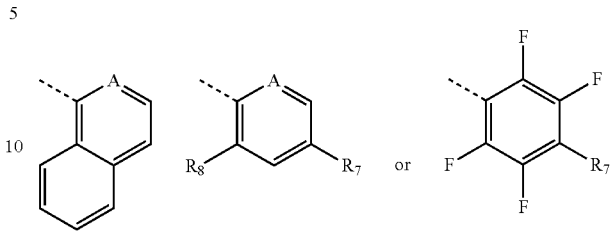

wherein
  A is CH or N;
  $R_7$ is H, NO$_2$, or CF$_3$; and
  $R_8$ is H or Cl;
or a salt, or a hydrate, or a solvate of any of the foregoing.

2. The compound of claim 1, wherein the compound is

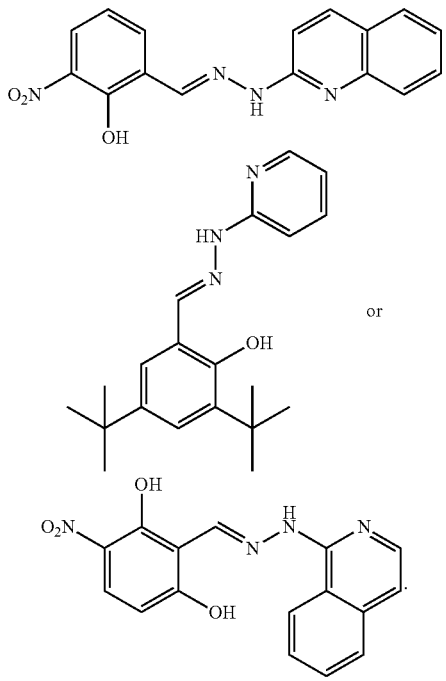

3. An isolated compound consisting of Formula I

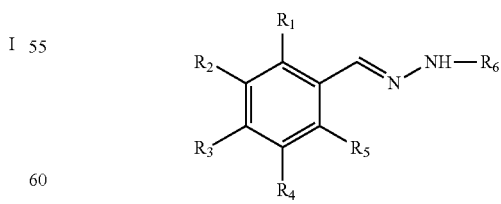

wherein:
  $R_1$ is OH, Cl, or methoxy;
  $R_2$ is H, NO$_2$, t-butyl or methoxy;
  $R_3$ is methyl, or t-butyl;
  $R_4$ is H, t-butyl, or methyl $R_5$ is H, Cl, or OH; and
wherein $R_6$ is

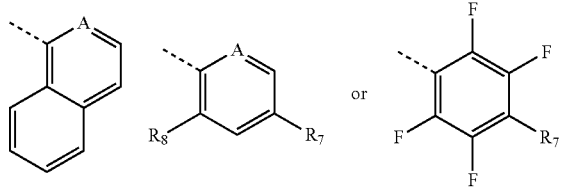

A is CH or N;
$R_7$ is H, $NO_2$, or $CF_3$; and
$R_8$ is H or Cl;
or a salt, or a hydrate, or a solvate of any of the foregoing.

4. The compound of claim 3, wherein the compound consists of

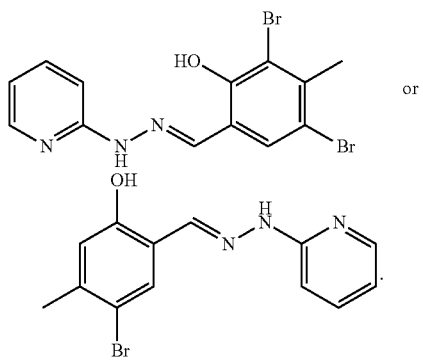

5. An isolated compound consisting of Formula I

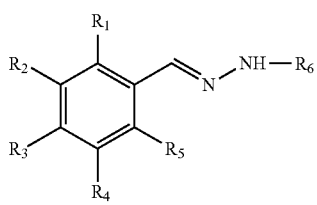

wherein:
$R_1$ is OH, Cl, or methoxy;
$R_2$ is H, $NO_2$, t-butyl or methoxy;
$R_3$ is H, methyl, or t-butyl;
$R_4$ is t-butyl, or methyl
$R_5$ is H, Cl, or OH; and
$R_6$ is

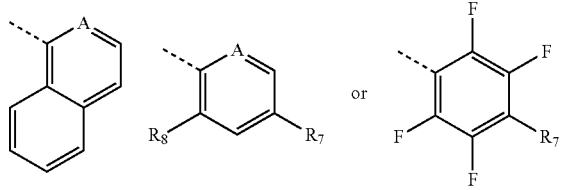

wherein
A is CH or N;
$R_7$ is H, $NO_2$, or $CF_3$; and
$R_8$ is H or Cl;
or a salt, or a hydrate, or a solvate of any of the foregoing.

6. The compound of claim 5, wherein the compound is

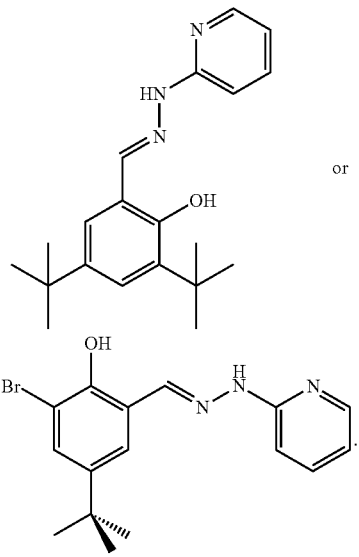

7. An isolated compound consisting of Formula I

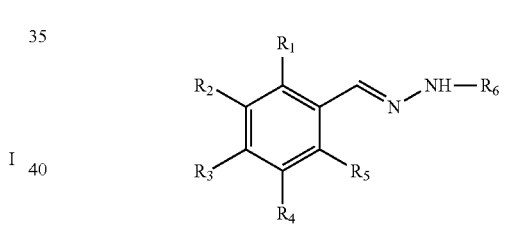

wherein:
$R_1$ is OH, Cl, or methoxy;
$R_2$ is H, $NO_2$, Br, Cl, t-butyl or methoxy;
$R_3$ is H, methyl, or t-butyl;
$R_4$ is H, Cl, Br, t-butyl, or methyl
$R_5$ is H, Cl, or OH; and
$R_6$ is

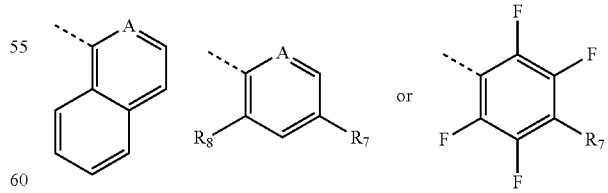

wherein
A is CH or N;
$R_7$ is $CF_3$; and
$R_8$ is H or Cl;
or a salt, or a hydrate, or a solvate of any of the foregoing.

8. The isolated compound of claim 7, wherein the compound consists of

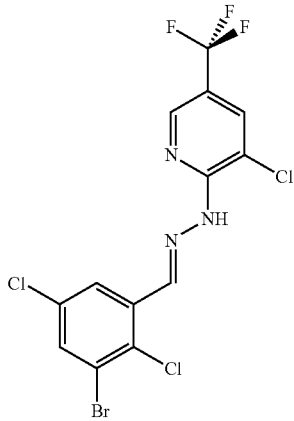

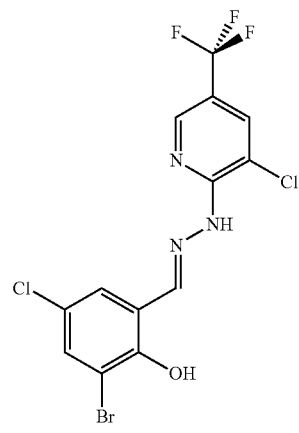

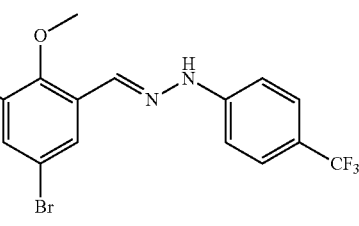

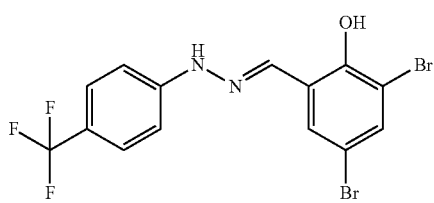

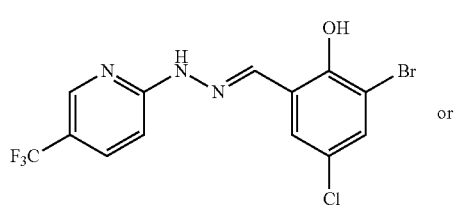

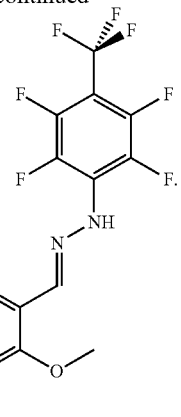

9. An isolated compound consisting of Formula I

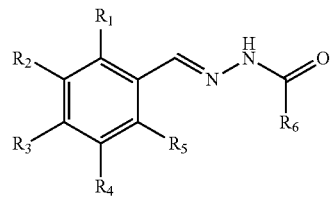

wherein:
R₁ is OH, Cl, or methoxy;
R₂ is H, NO₂, Br, Cl, t-butyl or methoxy;
R₃ is H, methyl, or t-butyl;
R₄ is H, Cl, Br, t-butyl, or methyl
R₅ is H, Cl, or OH; and
R₆ is

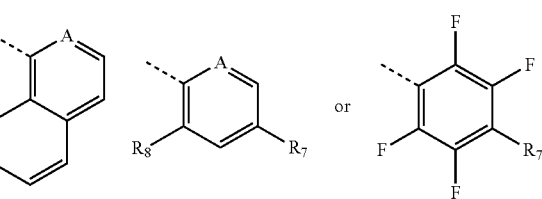

A is CH or N;
R₇ is H, NO₂, or CF₃; and
R₈ is H or Cl;
or a salt, or a hydrate, or a solvate of any of the foregoing.

10. The compound of claim 9, wherein the compound is

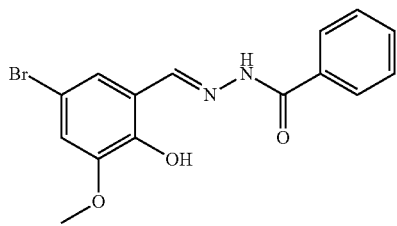

61
-continued
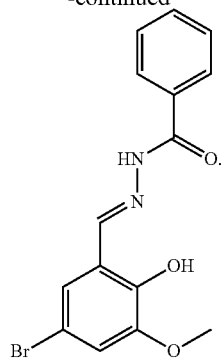
62
-continued
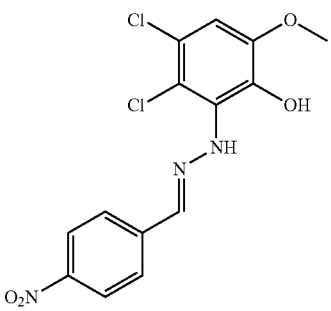
or
11. An isolated compound consisting of
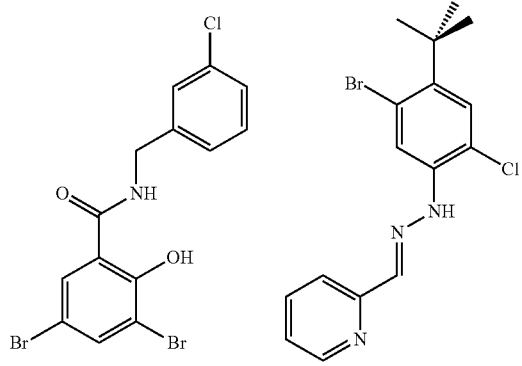
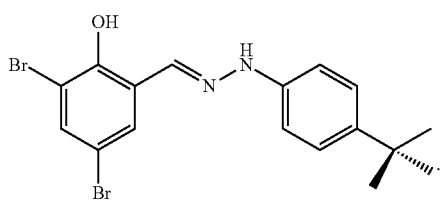
* * * * *